(12) United States Patent
Stensen et al.

(10) Patent No.: US 9,085,608 B2
(45) Date of Patent: Jul. 21, 2015

(54) TREATMENT OF BIOFILMS

(75) Inventors: Wenche Stensen, Kvaloysletta (NO); Frederick Alan Leeson, Tromso (NO); Stig Olov Magnus Engqvist, Tromso (NO); Trond Flægstad, Kvaloysletta (NO); Øystein Rekdal, Tromso (NO); John Sigurd Svendsen, Kvaloysletta (NO)

(73) Assignee: LYTIX BIOPHARMA AS, Tromso (NO)

( * ) Notice: Subject to any disclaimer, the term of this patent is extended or adjusted under 35 U.S.C. 154(b) by 600 days.

(21) Appl. No.: 13/122,177

(22) PCT Filed: Oct. 2, 2009

(86) PCT No.: PCT/GB2009/002364
§ 371 (c)(1),
(2), (4) Date: Jun. 20, 2011

(87) PCT Pub. No.: WO2010/038040
PCT Pub. Date: Apr. 8, 2010

(65) Prior Publication Data
US 2011/0236453 A1   Sep. 29, 2011

(30) Foreign Application Priority Data
Oct. 2, 2008   (GB) .................. 0818074.7

(51) Int. Cl.
| C07K 17/00 | (2006.01) |
| C07K 5/09 | (2006.01) |
| A61K 38/05 | (2006.01) |
| A61K 38/06 | (2006.01) |
| A61K 38/07 | (2006.01) |
| A61K 38/08 | (2006.01) |

(52) U.S. Cl.
CPC .............. *C07K 5/0817* (2013.01); *A61K 38/05* (2013.01); *A61K 38/06* (2013.01); *A61K 38/07* (2013.01); *A61K 38/08* (2013.01); *C07K 17/00* (2013.01)

(58) Field of Classification Search
None
See application file for complete search history.

(56) References Cited

U.S. PATENT DOCUMENTS

2003/0050247 A1* 3/2003 Kuhner et al. ............. 514/16
2003/0195144 A1* 10/2003 Svendsen et al. ............ 514/8

FOREIGN PATENT DOCUMENTS

| EP | 0801082 A2 * | 10/1997 |
| EP | 1967582 A1 | 9/2008 |
| JP | 2004-209241 | 7/2004 |
| JP | 2005-318829 | 11/2005 |
| JP | 2006511797 | 4/2006 |
| WO | 0198362 A2 | 12/2001 |
| WO | 2004058946 A2 | 7/2004 |
| WO | 2007074747 | 7/2007 |
| WO | 2007095393 | 8/2007 |
| WO | 2007130453 | 11/2007 |
| WO | 2007136354 A1 | 11/2007 |
| WO | WO-2009081151 A2 | 7/2009 |
| WO | WO-2009081152 A2 | 7/2009 |
| WO | WO-2010038041 A1 | 4/2010 |

OTHER PUBLICATIONS

Svenson et al., "Altered Activity and Physiochemical Properties of Short Cationic Antimicrobial Peptides by Incorporation of Arginine Analogues", Molecular Pharmaceutics, published on the web Apr. 2, 2009; pp. 996-1005.*

Sun et al. ,"Carbohydrate and Protein Immobilization on Solid Surfaces by Sequential Diels-Alder and Azide-Alkyene Cycoladditions", Bioconjugate Chemistry, 2006, pp. 52-57.*

Flemming et al., "High in vitro antimicrobial activity of synthetic antimicrobial peptidomimetics against staphylococcal biofilms", Journal of Antimicrobial Chemotherapy, advance access publication Nov. 14, 2008; pp. 136-145.*

Drobni, et al. "Multivariate design and evaluation of a set of RGRPQ-derived innate immunity peptides." J. Biol. Chem. 281(22): 15164-15171. (2006).

Haug, et al. "Bulky nonproteinogenic amino acids permit the design of very small and effective cationic antibacterial peptides." Journal of Medicinal Chemistry 47(17): 4159-4162. (2004).

Haug, et al. "Synthetic antimicrobial peptidomimetics with therapeutic potential." Journal of Medicinal Chemistry 51 (14): 4306-4314. (2008).

Singh, et al. "A component of innate immunity prevents bacterial biofilm development." Nature 417(6888): 552-555. (2002).

Beckloff et al, "Activity of an Antimicrobial Peptide Mimetic against Planktonic and Biofilm Cultures of Oral Pathogens" Antimicrob. Agents Chemother. 51 (2007), 4125-32.

Ostresh et al. ""Libraries from libraries": chemical transformation of combinatorial libraries to extend the range and repertoire of chemical diversity." PNAS, 91 (1994) 11138-42.

Wei et al, "Effect of MUC7 peptides on the growth of bacteria and on *Streptococcus mutans* biofilm," JAC, 57 (2006) 1100-9.

Altman et al, "In vitro assessment of antimicrobial peptides as potential agents against several oral bacteria." JAC, 58, (2006) 198-201.

(Continued)

*Primary Examiner* — Karlheinz R Skowronek
*Assistant Examiner* — Lianko Garyu
(74) *Attorney, Agent, or Firm* — Fox Rothschild LLP

(57) ABSTRACT

The present invention relates to a peptide or peptidomimetic for use in the treatment of a biofilm-associated infection in a subject, wherein said peptide or peptidomimetic a) carries a net positive charge, —b) is 1 to 6 amino acids in length or is an equivalently sized peptidomimetic; and c) is amphipathic in nature, having one or more lipophilic groups, one of said lipophilic groups comprising at least 7 non-hydrogen atoms.

23 Claims, 9 Drawing Sheets

(56) References Cited

OTHER PUBLICATIONS

Eckert et al, "Targeted killing of *Streptococcus mutans* by a pheromone-guided "smart" Antimicrobial Peptide." Antimicrob. Agents Chemother., 50, (2006) 3651-7.

Lasa, I., "Towards the identification of the common features of bacterial biofilm development." Internatl. Microbiol. 9, (2006) 21-8.
Donlan et al, "Biofilms: Survival Mechanisms of Clinically Relevant Microorganisms." Clin. Microbiol. Rev., 15, (2002) 167-93.

* cited by examiner

Structure 1

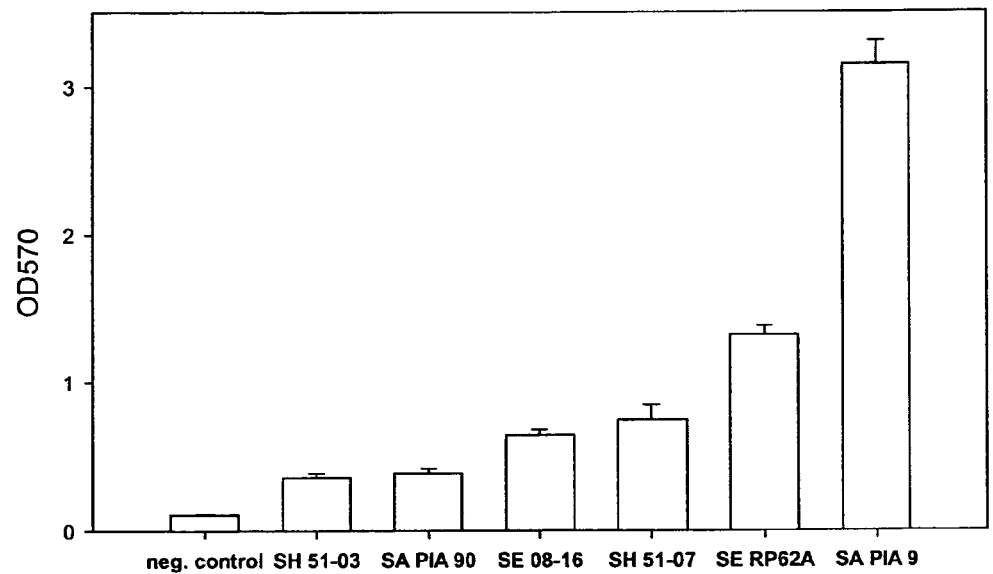
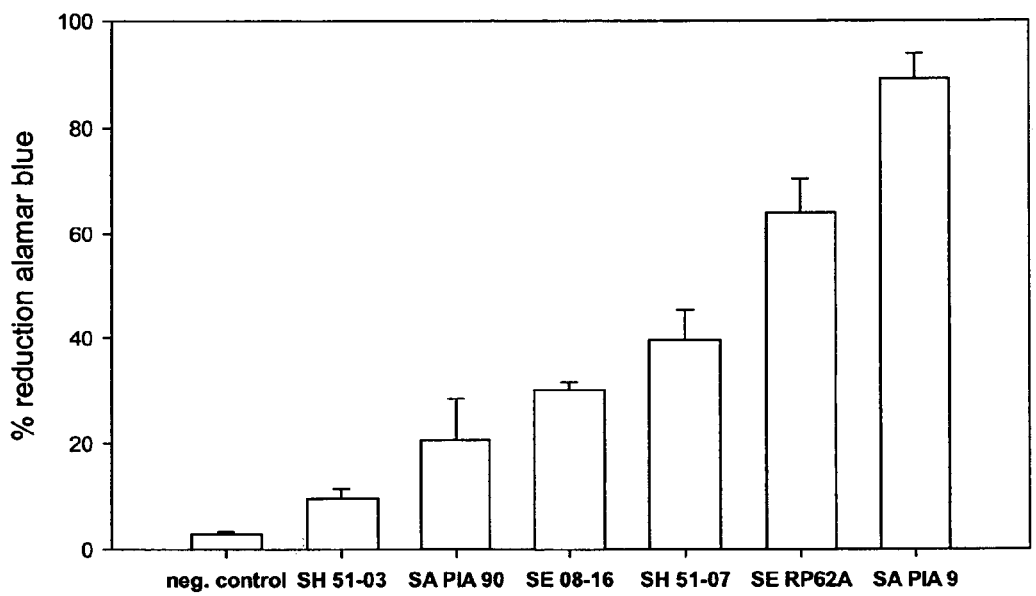
Figure 2

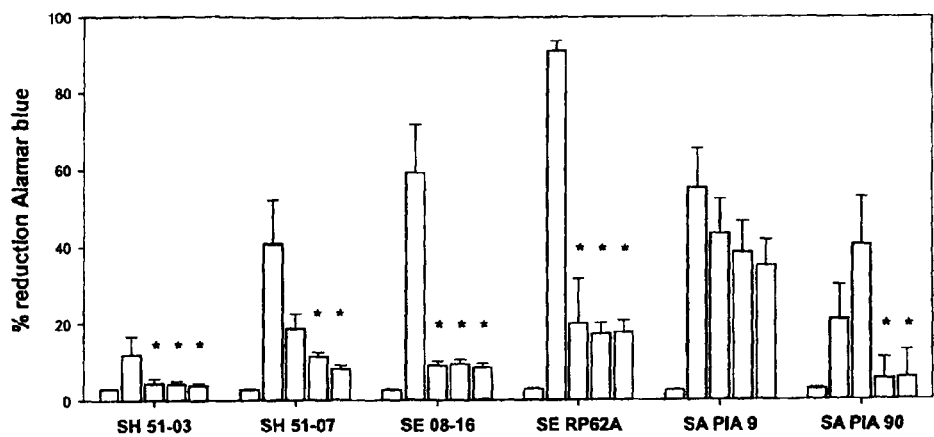
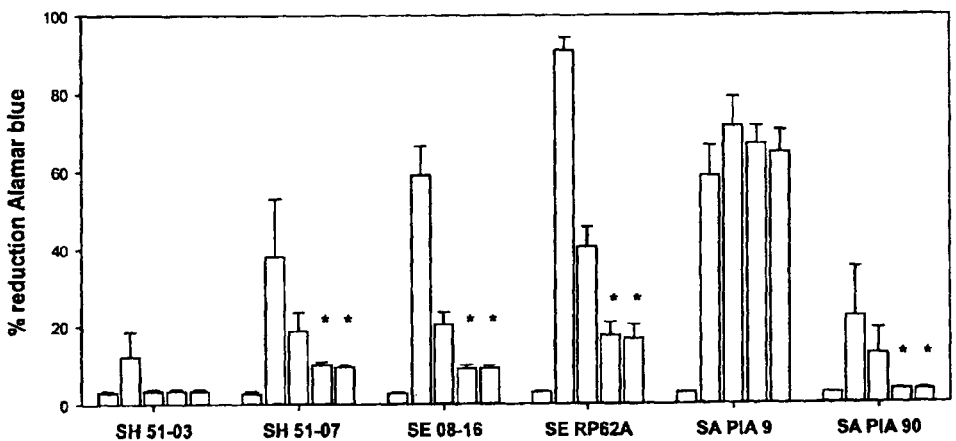
Figure 3 A and B

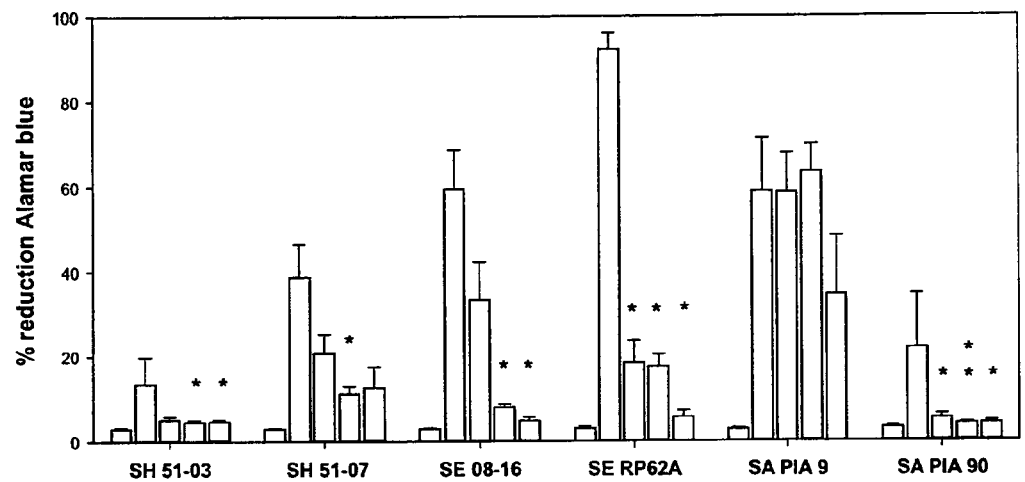
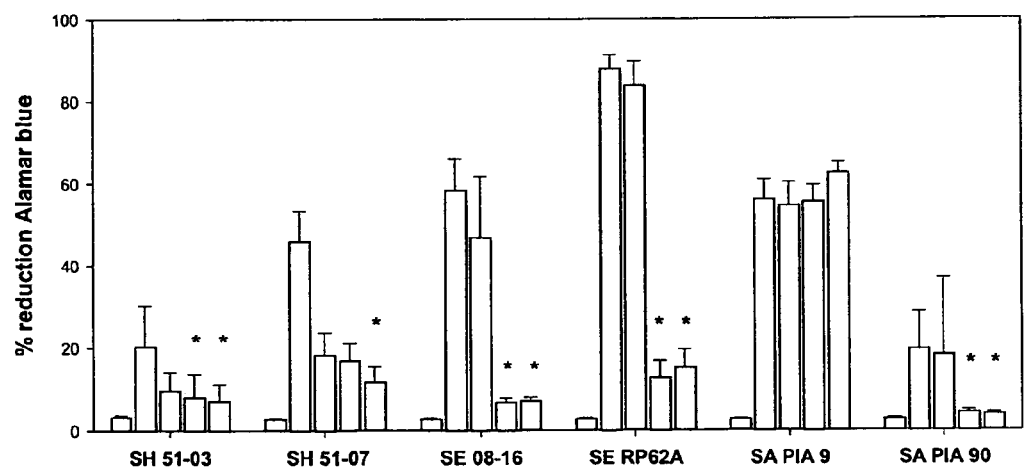
Figure 3 C and D

A
Compound A
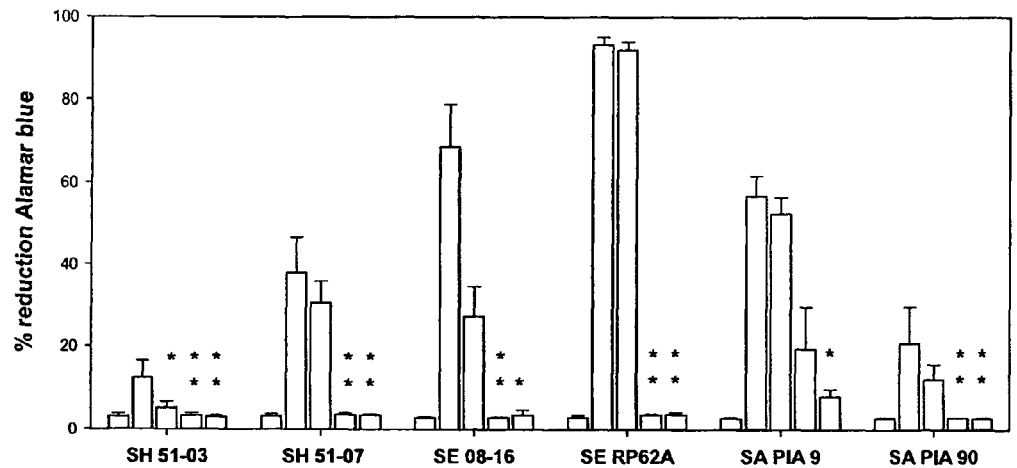
B
Compound B
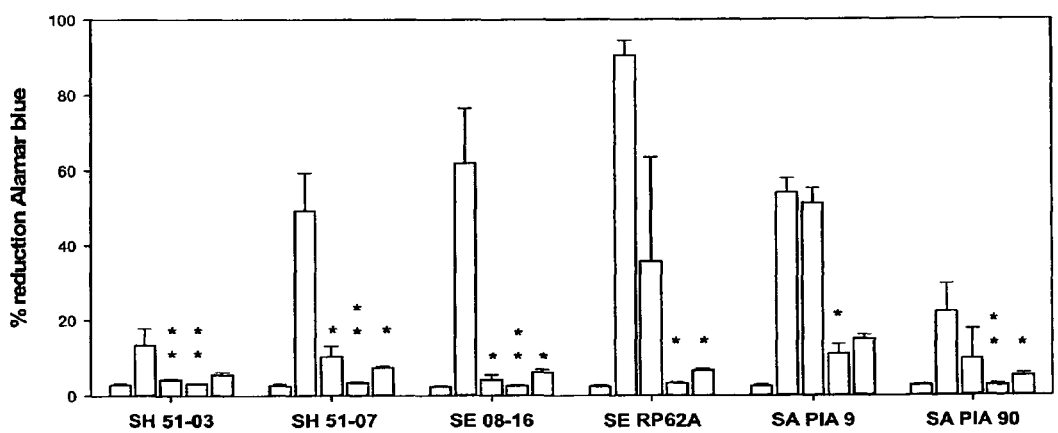
Figure 4 A and B

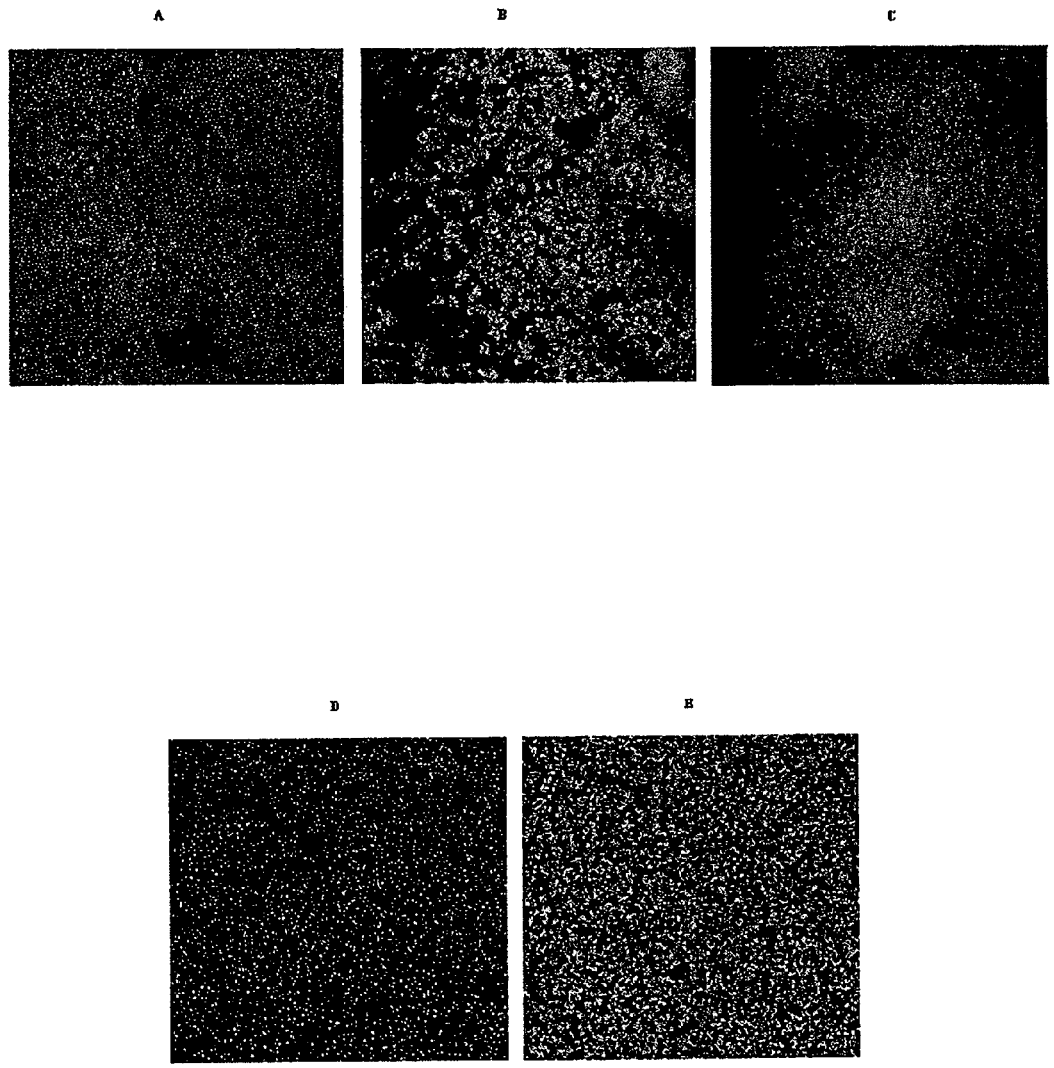
Figure 5 A-E

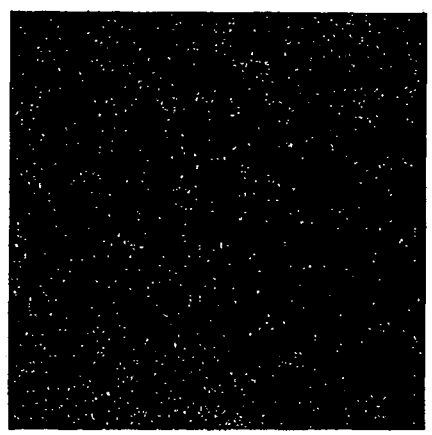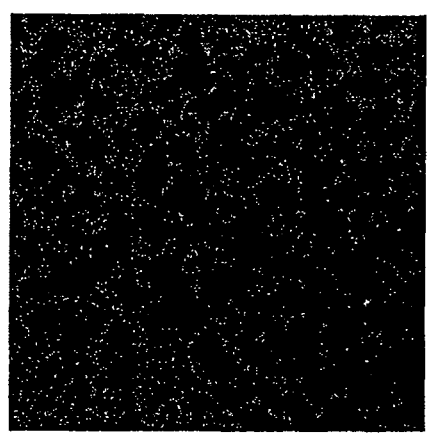
Figure 5 F and G

TREATMENT OF BIOFILMS

The present application is the U.S. National Phase of International Patent Application Serial No. PCT/GB2009/002364, filed Oct. 2, 2009, which claims the benefit of United Kingdom Patent Application Serial No. 0818074.7, filed Oct. 2, 2008, the disclosures of which are hereby incorporated by reference in their entireties.

The present invention relates to methods of treating biofilm-associated infections and to inhibiting biofilm formation or removing a biofilm in medical and environmental contexts. In particular, the invention relates to the use of lytic peptides and peptidomimetics in said methods.

In general terms a biofilm is a collection, or community, of microorganisms surrounded by a matrix of extracellular polymers (also known in the art as a glycocalyx). These extracellular polymers are typically polysaccharides, notably polysaccharides produced by the organisms themselves, but they can contain other biopolymers as well. A biofilm will typically be attached to a surface, which may be inert or living, but it has also been observed that biofilms may form from microorganisms attached to each other or at any interface. Such a mode of growth is protective to the microorganisms, and renders them difficult to remove or eradicate. Biofilms cause significant commercial, industrial and medical problems, in terms of infections, contamination, fouling and spoilage etc.

The microorganisms in a biofilm community display properties at the cellular level (phenotype) that are not shared by their planktonic (free-floating) equivalents. It is believed that such sessile microorganisms are profoundly different from planktonic free-floating cells. Further differences can be also be observed at the community level and are attributed to the effects of the extracellular matrix. Perhaps most notable is the commonly observed phenomenon that microorganisms in a biofilm environment do not display the same susceptibilities to anti-microbial agents, e.g. antibiotics, antifungals and microbicides, and host immune defenses or clearance mechanisms. It is thought that this resistance is due to the barrier effect of the extracellular matrix and/or a phenotypic change in the microbes themselves. It is also believed that microorganisms in biofilms may grow more slowly, and as a result take up anti-microbial agents more slowly.

Formation of a biofilm typically begins with the attachment of free-floating microorganisms to a surface. These first colonists may adhere to the surface initially through weak, reversible van der Waals forces. If the colonists are not immediately separated from the surface, they can anchor themselves more permanently using cell adhesion structures such as pili. The first colonists typically facilitate the arrival of other cells by providing more diverse adhesion sites and beginning to build the matrix that holds the biofilm together. Some species are not able to attach to a surface on their own but are often able to anchor themselves to the matrix or directly to earlier colonists. During this colonization the cells are able to communicate via quorum sensing. Once colonization has begun, the biofilm may grow through a combination of cell division and recruitment. The final stage of biofilm formation is known as development, and is the stage in which the biofilm is established and may only change in shape and size. This development of biofilm allows for the cells to become more antibiotic resistant. A biofilm in the "development" stage may be referred to as a "mature" biofilm.

Biofilms form readily on surfaces and an established microbial colony on any surface exposed to water (any "wet" surface) could exist as a biofilm structure. Furthermore it is now becoming evident and increasingly documented that biofilms may also form in the case of microbial infections, i.e. within or on an infected host. Thus biofilm formation may also occur on a "physiological" surface, that is on an animate or biotic surface, or a surface on or in an infected host organism (e.g. a human or non-human animal subject), for example on an internal or external body or tissue surface. Such biofilm formation (or infection) on body tissues is increasingly believed to contribute to various infective diseases, including for example native valve endocarditis (mitral, aortic, tricupsid, pulmonic heart valves), acute otitis media (middle ear), chronic bacterial prostatitis (prostate), cystic fibrosis (lungs), pneumonia (respiratory tract), periodontitis (tissues supporting the teeth; e.g. gingiva, periodontal ligament, alvelor bone). Biofilm niches are present when medical devices are implanted and the formation of biofilm on such implanted ("in-dwelling") devices can lead to clinical problems with infection at such sites, such as prosthetic valve endocarditis and device-related infection, for example with intrauterine devices, contact lenses, prostheses (e.g. prosthetic joints) and at catheterisation sites, for example with central venous or urinary catheters.

A significant problem and risk with such biofilm infections is that microorganisms (or more particularly microcolonies) may break off or detach from the biofilm, and enter other tissues, including significantly the circulation. Such circulating biofilm-derived microorganisms can cause further infections and lead to significant clinical problems, particularly as the detached circulating microorganisms may have all the resistance characteristics of the parent community.

Body or tissue surfaces which are dead or damaged (e.g. necrotic or inflamed) are particularly susceptible to biofilm infection. Wounds are susceptible to infection and biofilm formation can occur in wounds that do not heal in a short amount of time. Wounds are an ideal environment for the formation of biofilms due to their susceptibility to contamination and the availability of substrate and surface for biofilm attachment. Problematically, infection of a wound often delays healing further and thus renders that wound more susceptible to biofilm formation and established infection. Chronic wounds in which healing is delayed represent sites of particular concern with respect to biofilm formation. A chronic wound is in an inflammatory state, with elevated levels of pro-inflammatory cytokines. The effect of these cytokines is to produce a swarming of the area with immune cells (neutrophils and macrophages). If this defense system is in any way delayed, bacteria or other microorganisms have time to attach to the surface and enter the biofilm mode of growth. Evidence is increasingly growing that both chronic and acute wounds may be sites of biofilm infection, with evidence of diverse microbial communities or populations in wounds, particularly chronic wounds, including anaerobic bacteria within chronic wounds. Chronic wound infections share two important attributes with other biofilm infections: persistent infection that is not cleared by the host immune system even in individuals with healthy innate and adaptive immune reactions, and resistance to systemic and topical antimicrobial agents. Accordingly, biofilm based infection is very difficult to treat and biofilm contamination is very difficult to eradicate.

Chronic wounds are a major health problem throughout the world and represent a significant drain on clinical resources. Three principle types of chronic wound are diabetic foot ulcers, venous leg ulcers and pressure ulcers, although other wounds, including surgical wounds, may become chronic. The care of such wound imposes enormous material and patient costs, and hence an effective anti-biofilm treatment, or indeed any treatment which assisted in or facilitated the treatment of biofilms, and thus accelerated or facilitated wound healing, would be of very significant impact.

More specifically, biofilms play a central role in the pathogenesis of serious-infections caused by *Staphylococcus aureus* and coagulase negative staphylococci (CONS), often implicated in chronic wound infections and medical device-related infections.

Bacteria grown in biofilms are more tolerant to antimicrobial agents than their planktonic counterparts. Susceptibility testing of planktonic bacteria may fail to predict in vivo resistance of device-related infections to antimicrobial agents.

Thus there is a need for agents which are active antimicrobials and able to exert their effect even against microbes which are existing as a biofilm.

The rising number of infections caused by bacterial isolates resistant to conventional antibiotics has lead to an intense search for novel antibiotics. Cationic antimicrobial peptides (CAPs) are widespread in nature and play an important role as part of innate immunity. In general, CAPs are fairly large molecules that carry a net positive charge and contain about 50% hydrophobic residues. Their mode of action involves binding to negatively charged structural molecules on the microbial membrane. Once bound, CAPs form pores that increase the cell membrane permeability and ultimately lead to cell lysis. There is also evidence for other antimicrobial mechanisms such as interaction with intracellular targets and activation of autolytic enzymes. CAPS have a broad spectrum of antimicrobial activity and development of resistance is rare. Modifications of CAPs have resulted in development of extremely short synthetic antimicrobial peptidomimetics, called SAMPs (Haug et al. [2008] J. Med. Chem. 51, 4306-4314). SAMPs mimic the effect of CAPs, but may have improved pharmacokinetic properties.

Beckloff et al. in Antimicrobial Agents and Chemotherapy [2007] p 4125-4132 describe the use of a small molecule, meta-phenylene ethynylene as an active against biofilm but this molecule is structurally very different from the peptide based molecules of use according to the present invention.

The present inventors have found that certain CAP type molecules and SAMPs have exceptional activity as anti-biofilm agents.

Thus, in one aspect, the present invention provides a peptide or peptidomimetic which:
a) carries a net positive charge;
b) is 1 to 6, preferably at least 1 or 2 and up to 4, 5 or 6, e.g. 2 to 5 or 2 to 6 amino acids in length or an equivalently sized peptidomimetic; and
c) is amphipathic in nature, having one or more lipophilic groups, one of said lipophilic groups comprising at least 7 non-hydrogen atoms;
for use in treating a biofilm-associated infection.

By "biofilm" it is meant a sessile community of microorganisms characterized by cells that are attached to a substratum or interface or to each other, that are embedded in a matrix of extracellular polymers (more specifically extracellular polymers that they have produced), and that exhibit an altered phenotype with respect to growth rate and gene transcription (for example as, compared to their "non-biofilm" or free-floating or planktonic counterparts).

The prevalence of biofilms in bacterial infections which are problematic for human and non-human animal subjects is now being appreciated. They are especially implicated in chronic wound infections and medical device-related infections. Thus in a preferred embodiment the invention provides the peptides and peptidomimetics defined herein for use in the treatment of a biofilm associated with a chronic wound infection or a biofilm associated with a medical device-related infection.

Alternatively viewed, the present invention provides the use of a peptide or peptidomimetic as defined herein in the manufacture of a medicament for treating a biofilm-associated infection.

Alternatively viewed, the present invention provides a method of treating a biofilm-associated infection in a subject which comprises administering thereto a peptide or peptidomimetic as defined herein.

A "biofilm-associated infection" is a microbial infection of a subject where it is known or suspected that the microbes are present as a biofilm. Typically it will be an infection where the existence of a biofilm is relevant to the clinical condition, e.g. to the diagnosis or prognosis, to the treatment regimen, to the severity of the infection, to the duration of the infection up to the point of treatment or anticipated in the future. 'Treatment' includes prophylactic treatment and encompasses a reduction in size of the biofilm, a reduction in number of living microorganisms within the biofilm and prevention or reduction in the tendency of microorganisms within the biofilm to break free and form new biofilm colonies. Treatment includes an improvement, observed by clinician or patient, in one or more of the symptoms associated with the infection.

The size, structure, integrity, and number of microbes in a biofilm can be analysed by any convenient method. For instance, scanning and transmission electronic microscopy is often used to asses the size, integrity and structure of a biofilm. Analysis of biofilm is described in the Examples hereto.

The biofilms that may be treated in accordance with the invention are not limited in terms of the microorganisms they contain, the lytic molecules described herein target the cell membranes and therefore have a fairly non-specific activity. Accordingly, the biofilm may comprise any class, genus or species of microorganism, namely any microorganism that may form a biofilm. Such microorganisms typically include bacteria, including any genus or species of bacteria. Thus, the bacteria may be gram positive or gram negative, or gram test non-responsive. They may be aerobic or anaerobic. The bacteria may be pathogenic or non-pathogenic.

It is particularly surprising that the molecules defined herein are able to kill bacteria in mature biofilms and the treatment of such biofilms is particularly preferred.

The biofilm may comprise Gram positive bacteria, *Pseudomonas aeruginosa* and/or fungi. Biofilms comprising or consisting of Gram positive bacteria are preferred targets.

Biofilms comprising *Staphylococcus* are preferred targets, with biofilms comprising *S. haemolyticus* being especially preferred.

Biofilms may also contain fungi, algae and other organisms such as parasitic protozoa. Mixed colony biofilms are known and treatable according to the methods described herein.

Chronic wounds are discussed above and are a preferred therapeutic target, these include diabetic foot ulcers, venous leg ulcers and pressure ulcers as well as surgical wounds (postoperative wound infections) which have become chronic.

Medical devices are a particular class of surface on which a biofilm may form and represent a further preferred therapeutic target according to the present invention.

This may include any kind of line, including catheters (e.g. central venous and urinary catheters), prosthetic devices e.g., heart valves, artificial joints, false teeth, dental crowns, dental caps and soft tissue implants). Any kind of implantable (or "in-dwelling") medical device is included (e.g. stents, intrauterine devices, pacemakers, intubation tubes, prostheses or prosthetic devices, lines or catheters). An "in-dwelling" medical device may include a device in which any part of it is contained within the body, i.e. the device may be wholly or partly in-dwelling.

In specific embodiments of the invention the peptides and peptidomimetics may be used in the treatment of native valve endocarditis, acute otitis media, chronic bacterial prostatitis, pneumonia, dental plaque, periodontitis, biofilm infections in respiratory diseases, which may include cystic fibrosis, and device related infection associated with implantable or prosthetic medical devices e.g. prosthetic valve endocarditis or infection of lines or catheters or artificial joints or tissue replacements.

The wounds may be acute or chronic. Acute wounds are wounds that proceed orderly through the three recognised stages of the healing process (i.e. the inflammatory stage, the proliferative stage and the remodelling phase) without a protracted time course. Chronic wounds, however, are those wounds that do not complete the ordered sequence of biochemical events because the wound has stalled in one of the healing stages. Viewed alternatively a chronic wound is a wound that has not healed within at least 40 days, preferably at least 50 days, more preferably at least 60 days, most preferably at least 70 days.

The wound to be treated may be a breach in, or denudement of, the tissue for instance caused by surgical incision or trauma, e.g., mechanical, thermal, electrical, chemical or radiation trauma; a spontaneously forming lesion such as a skin ulcer (e.g. a venous, diabetic or pressure ulcer); a blister (e.g. a friction or thermal blister or a blister caused by pathogen infection such as chicken pox); an anal fissure or a mouth ulcer.

The treatment of chronic wounds represents a particularly preferred aspect of the present invention.

Although biofilms are now more widely recognised as contributing to medical conditions, they are also implicated in non-medical problems caused by microbial colonisation of surfaces. This may be, for example, in domestic, industrial, research or hospital settings where surfaces need to be kept free of bacterial contamination.

As noted above the biofilm may be present on a surface. The surface is not limited and includes any surface on which a microorganism may occur, particularly, as noted above, a surface exposed to water or moisture. The surface may be biotic or abiotic, and inanimate (or abiotic) surfaces include any such surface which may be exposed to microbial contact or contamination. Thus particularly included are surfaces on machinery, notably industrial machinery, or any surface exposed to an aquatic environment (e.g. marine equipment, or ships or boats or their parts or components), or any surface exposed to any part of the environment e.g. pipes or on buildings. Such inanimate surfaces exposed to microbial contact or contamination include in particular any part of: food or drink processing, preparation, storage or dispensing machinery or equipment, air conditioning apparatus, industrial machinery e.g. in chemical or biotechnological processing plants, storage tanks and medical or surgical equipment. Any apparatus or equipment for carrying or transporting or delivering materials, which may be exposed to water or moisture is susceptible to biofilm formation. Such surfaces will include particularly pipes (which term is used broadly herein to include any conduit or line). Representative inanimate or abiotic surfaces include, but are not limited to food processing, storage, dispensing or preparation equipment or surfaces, tanks, conveyors, floors, drains, coolers, freezers, equipment surfaces, walls, valves, belts, pipes, air conditioning conduits, cooling apparatus, food or drink dispensing lines, heat exchangers, boat hulls or any part of a boat's structure that is exposed to water, dental waterlines, oil drilling conduits, contact lenses and storage cases.

Thus in a further aspect the present invention provides a method of inhibiting biofilm formation or removing a biofilm which comprises contacting said biofilm with a peptide or peptidomimetic as defined herein. Said biofilm may be on any of the surfaces described above.

The term "contacting" encompasses any means of delivering the peptide or peptidomimetic to the biofilm, whether directly or indirectly, and thus any means of applying the peptide or mimetic to the biofilm or exposing the biofilm to the peptide or mimetic e.g. applying the peptide or mimetic directly to the biofilm.

The peptide or peptidomimetic will advantageously have a net charge of at least plus 2 or plus 3.

Preferred peptides are 2 to 4 amino acids in length, most preferably 3 amino acids in length.

Preferred peptidomimetics are equivalently sized and, where preferred features of peptides are described such features are, mutatis mutandis, preferred features of the peptidomimetics.

The molecules will preferably have a lipophilic group which has at least 9, 10, 11 or 12 non-hydrogen atoms. Where a molecule incorporates a lipophilic group of only 7 or 8 non-hydrogen atoms the molecule will preferably include a further lipophilic group of at least 3, typically at least 6 non-hydrogen atoms.

The largest lipophilic group will typically be an amino acid R group but may be present as part of an N or preferably C terminal modification. Suitable genetically coded amino acids providing said lipophilic group are phenylalanine (7 non-hydrogen atoms), tryptophan (10 non-hydrogen atoms) and tyrosine (8 non-hydrogen atoms). From hereon when referring to amino acids, standard single-letter amino acid abbreviations or standard three-letter amino acid codes may be used.

One of the lipophilic groups will usually include a cyclic group which may be aromatic; a lipophilic group having 2 cyclic groups, which may or may not be fused, is preferred. The lipophilic group may contain hetero atoms such as O, N, S or F but typically there is no more than one heteroatom, preferably it is nitrogen. The lipophilic group will preferably have no more than 2 polar groups, more preferably none or one, most preferably none.

Preferred non-genetic amino acids providing said lipophilic group are tributyl tryptophan (Tbt), biphenylalanine or diphenylalanine or a biphenylalanine derivative such as Bip (4-(2-Naphthyl)), Bip(4-(1-Naphthyl)), Bip(4-n-Bu), Bip(4-Ph) or Bip(4-T-Bu) or Phe(4-(2'-naphthyl)), Phe(4-(1'-naphthyl)), Phe(4-n-butylphenyl), Phe(4-4'-biphenyl) or Phe(4'-t-butylphenyl).

The peptides will typically comprise 1, 2 or 3 cationic amino acids, preferably 2 cationic amino acids, preferably lysine or arginine but possibly histidine or any non-genetically coded or modified amino acid carrying a positive charge at pH 7.0.

Suitable non-genetically coded amino acids and modified amino acids which can provide a cationic amino acid include analogues of lysine, arginine and histidine such as homolysine, ornithine, diaminobutyric acid, diaminopimelic acid, diaminopropionic acid and homoarginine as well as trimethylysine and trimethylornithine, 4-aminopiperidine-4-carboxylic acid, 4-amino-1-carbamimidoylpiperidine-4-carboxylic acid and 4-guanidinophenylalanine.

Preferred molecules for use according to the present invention are compounds, preferably peptides, comprising 3 amino acids moieties, wherein in any order, 2 of said amino acid moieties are cationic amino acids, preferably lysine or arginine but may be histidine or any non-genetically coded or modified amino acid carrying a positive charge at pH 7.0, and 1 of said amino acids is an amino acid with a large lipophilic R group, the R group having 14-27 non-hydrogen atoms and preferably containing 2 or more, e.g. 2 or 3, cyclic groups which may be fused or connected, these cyclic groups will typically comprise 5 or 6 non-hydrogen atoms, preferably 6 non-hydrogen atoms. In the case of fused rings or course the non-hydrogen atoms may be shared.

These preferred compounds may be 3 amino acids in length, i.e. a tripeptide. However, also included are compounds which are up to 6 amino acids in length, preferably 4 or 5 amino acids in length. Compounds which are greater than 3 amino acids in length may comprise additional amino acids at the N and/or the C terminus of the tripeptide. Alternatively, or in addition, the compounds which are greater than 3 amino acids in length may comprise the amino acids of the tripeptide described above separated in linear sequence by one or more further amino acids.

Preferably, when the compounds are greater than 3 amino acids in length the further amino acids are either cationic or lipophilic amino acids. A peptide of 4 amino acids in length will typically comprise 2 cationic and 2 lipophilic amino acids; a peptide of 5 amino acids in length will typically comprise 3 cationic and 2 lipophilic amino acids or 2 cationic and 3 lipophilic amino acids. A preferred group of compounds greater, than 3 amino acids in length have phenylalanine as their C-terminal amino acid.

Optionally, the compounds of use in the present invention may be attached to a solid support in order to prevent the formation of a biofilm thereon or in the environment around the solid support. In the context of the present invention, the terms "solid support" and "surface" are, interchangeable.

Thus, in a further aspect is provided a solid support having attached thereto a compound as described herein of use according to the present invention. Such solid supports include but are not limited to the surfaces described above. Surfaces on which biofilms can form include medical devices, containers, carriers or ducts carrying water or other fluids etc. Medical devices are a particular class of surface on which a biofilm may form and represent a preferred surface onto which the compounds of use in the present invention are attached.

The term "medical devices" includes any kind of line, including catheters (e.g. central venous and urinary catheters), prosthetic devices e.g., heart valves, artificial joints, false teeth, dental crowns, dental caps and soft tissue implants). Any kind of implantable (or "in-dwelling") medical device is included (e.g. stents, intrauterine devices, pacemakers, intubation tubes, prostheses or prosthetic devices, lines or catheters). An "in-dwelling" medical device may include a device in which any part of it is contained within the body, i.e. the device may be wholly or partly in-dwelling.

The compounds of use in the present invention can be attached to solid supports by any means known in the art. The compounds may be directly or indirectly attached to the solid support, i.e. they may be attached by a linking group. Preferably the compounds are directly attached to the solid support although, as discussed below, modification of the compounds may be required to permit attachment. Typically, the compounds are covalently attached to a desired solid support. Therefore, optionally the compounds of use in the present invention comprise a chemical group which permits covalent attachment to said solid support. Alternatively, the compounds are modified to permit covalent attachment to said solid support.

The term "modified" or "modification" includes the replacement of a chemical group of a compound of use in the present invention for a chemical group which permits covalent attachment to said support. The term also includes the further substitution of an existing chemical group with a chemical group which permits covalent attachment to said support. The term also includes the scenario where, rather than replacing or further substituting a chemical group of a pre-existing compound of use in the present invention, the compound is designed to comprise such a chemical group which permits covalent attachment to said solid support, and is prepared in this form.

The exact nature of the chemical group which permits covalent attachment to the support will depend on the chemical nature of the desired surface to which the compound is being attached. Likewise, the surface of the solid support may be modified to enable attachment. A variety of suitable chemical groups are well-known in the art and the appropriate groups for attachment would be readily determinable by the skilled man. By way of example only, chemical groups which permit covalent attachment to surfaces may be heteroatom-containing groups, including oxygen-containing groups such as carboxyl groups, nitrogen-containing groups such as amide groups and sulphur-containing groups such as thiol groups. Covalent bonds which can exist between the compounds of use in the invention and the desired supports include but are not limited to ether, ester amide, amine, sulfide, thioether and thioester bonds. Thus, for example, an ester link may have been formed from an alcohol moiety on the support and a carboxylic acid moiety within the compound of use in the invention or vice versa. Alternatively, covalent attachment of the compound of use in the invention to surfaces may be achieved via connections which do not involve heteroatoms, for instance utilising alkene or vinyl groups, wherein either the alkene or vinyl group is within the compound of use in the invention and the other necessary group is on a desired surface. Cycloaddition reactions may also be used to covalently attach the compounds of use in the invention to a desired surface.

Preferably, said covalent attachment is between the C-terminus of the compound and the support. Thus, preferably, the compound contains, or is modified to contain at its C-terminus a chemical group which permits covalent attachment to the support.

Optionally, the modification is the incorporation at the C-terminus of one or more lipophilic groups which contain a chemical group which permits covalent bonding to said support. For example the lipophilic group, in the form as it is attached, may be selected from the group consisting of —NHCH(CH$_3$)CO—, —NH(CH$_2$)$_5$CO—, —NH(CH2)$_3$CO—, —NH(CH$_2$)$_2$CO— and —NHCH$_2$CH(CH$_3$)CO—, and most preferably is —NHCH(CH$_3$)CO— or —NH(CH$_2$)$_5$CO—. The carboxyl groups of these groups permits the covalent attachment of the compound to a support.

Preferred molecules are those defined in WO 01/66147, the contents of which are incorporated herein by reference.

A group of especially preferred molecules are described in GB 0724951.9, the contents of which are also incorporated herein by reference.

Thus preferred molecules for use according to the present invention are compounds, preferably peptides, of formula (I)

AA-AA-AA-X—Y—Z  (I)

wherein, in any order, 2 of said AA (amino acid) moieties are cationic amino acids, preferably lysine or arginine but may be histidine or any non-genetically coded or modified amino acid carrying a positive charge at pH 7.0, and 1 of said AA is an amino acid with a large lipophilic R group, the R group having 14-27 non-hydrogen atoms and preferably containing 2 or more, e.g. 2 or 3, cyclic groups which may be fused or connected, these cyclic groups will typically comprise 5 or 6 non-hydrogen atoms, preferably 6 non-hydrogen atoms;

X is a N atom, which may be but preferably is not substituted by a branched or unbranched $C_1$-$C_{10}$ alkyl or aryl group, e.g. methyl, ethyl or phenyl, and this group may incorporate up to 2 heteroatoms selected from N, O and S;

Y represents a group selected from —$R_a$—$R_b$—, —$R_a$—$R_b$—$R_b$— and —$R_b$—$R_b$—$R_a$— wherein $R_a$ is C, O, S, N or F, preferably C, and $R_b$ is C; each of $R_a$ and $R_b$ may be substituted by, for example, $C_1$-$C_4$ alkyl groups or carboxyl groups, or may be unsubstituted, preferably Y is —$R_a$—$R_b$— (in which $R_a$ is preferably C) and preferably this group is not substituted, when Y is —$R_a$—$R_b$—$R_b$— or $R_b$—$R_b$—$R_a$— then preferably one or more of $R_a$ and $R_b$ is substituted; and Z is a group comprising 1 to 3 cyclic groups each of 5 or 6 non-hydrogen atoms (preferably C atoms), 2 or more of the cyclic groups may be fused; one or more of the rings may be substituted and these substitutions may, but will typically not, include polar groups, suitable substituting group's include halogens, preferably fluorine and $C_1$-$C_4$ alkyl groups; the Z moiety incorporates a maximum of 15 non-hydrogen atoms, preferably 5-12, most preferably it is phenyl;

the bond between Y and Z is a covalent bond between $R_a$ or $R_b$ of Y and a non-hydrogen atom of one of the cyclic groups of Z.

In a particularly preferred embodiment the compounds, preferably peptides, are of formula (II)

$$AA_1\text{-}AA_2\text{-}AA_1\text{-}X\text{—}Y\text{—}Z \qquad (II)$$

wherein:

$AA_1$ is a cationic amino acid, preferably lysine or arginine but may be histidine or any non-genetically coded or modified amino acid carrying a positive charge at pH 7.0;

$AA_2$ is an amino acid with a large lipophilic R group, the R group having 14-27 non-hydrogen atoms and preferably containing 2 or more, e.g. 2 or 3, cyclic groups which may be fused or connected, these cyclic groups will typically comprise 5 or 6 non-hydrogen atoms, preferably 6 non-hydrogen atoms; and X, Y and Z are as defined above.

Further useful compounds include compounds of formulae (III) and (IV):

$$AA_2\text{-}AA_1\text{-}AA_1\text{-}X\text{—}Y\text{—}Z \qquad (III)$$

$$AA_1\text{-}AA_1\text{-}AA_2\text{-}X\text{—}Y\text{—}Z \qquad (IV)$$

wherein $AA_1$, $AA_2$, X, Y and Z are as defined above.

From amongst the above compounds certain are preferred. In particular, compounds wherein the amino acid with a large lipophilic R group, conveniently referred to herein as $AA_2$, is tributyl tryptophan (Tbt) or a biphenylalanine derivative such as Bip(4-(2-Naphthyl)), Bip(4-(1-Naphthyl)), Bip(4-n-Bu), Bip(4-Ph) or Bip(4-T-Bu,), Bip(4-(2-Naphthyl)) and Tbt being most preferred. Another preferred group of compounds are those wherein Y is —$R_a$—$R_b$— as defined above, preferably wherein $R_a$ and $R_b$ are unsubstituted, most preferably wherein $R_a$ and $R_b$ are both carbon atoms.

A further preferred group of compounds are those in which —X—Y—Z together is the group —$NHCH_2CH_2Ph$.

The compounds include all enantiomeric forms, both D and L amino acids and enantiomers resulting from chiral centers within the amino acid R groups and moieties Y or Z.

Especially preferred compounds are the following:

Compound 1

Compound 2

A further group of preferred molecules for use according to the invention are compounds, preferably peptides, of formula (V)

$$AA\text{-}AA\text{-}AA\text{-}R_1\text{—}R_2 \qquad (V)$$

wherein, in any order, 2 of said AA (amino acid) moieties are cationic amino acids, preferably lysine or arginine but may be histidine or any non-genetically coded or modified amino acid carrying a positive charge at pH 7.0, and 1 of said AA is an amino acid with a large lipophilic R group, the R group having 14-27 non-hydrogen atoms and preferably containing 2 or more, e.g. 2 or 3, cyclic groups which may be fused or connected, these cyclic groups will typically comprise 5 or 6 non-hydrogen atoms, preferably 6 non-hydrogen atoms;

$R_1$ is a N atom, which may be but preferably is not substituted by a branched or unbranched $C_1$-$C_{10}$ alkyl or aryl group, e.g. methyl, ethyl or phenyl, and this group may incorporate up to 2 heteroatoms selected from N, O, S and F, F being the least preferred;

$R_2$ is an aliphatic moiety having 2-20 non-hydrogen atoms, preferably these are carbon atoms but oxygen, nitrogen or sulphur atoms may be incorporated, preferably $R_2$ comprises 3-10, most preferably 3-6 non-hydrogen atoms and the moiety may be linear, branched or cyclic. If the $R_2$ group comprises a cyclic group this is preferably attached directly to the nitrogen atom of $R_1$.

Preferred compounds incorporate an $R_2$ group which is linear or branched, in particular a linear or branched alkyl group including ethyl, propyl, isopropyl, butyl, isobutyl, sec-butyl, tert-butyl, pentyl and isomers thereof, hexyl and isomers thereof etc., propyl, isopropyl, butyl and isobutyl are especially preferred.

Of the $R_2$ groups which comprise a cyclic group, preferred are molecules in which $R_2$ is cyclohexyl or cyclopentyl.

Suitable non-genetically coded amino acids and modified amino acids which can provide a cationic amino acid include analogues of lysine, arginine and histidine such as homolysine, ornithine, diaminobutyric acid, diaminopimelic acid, diaminopropionic acid and homoarginine as well as trimethylysine and trimethylornithine, 4-aminopiperidine-4-carboxylic acid, 4-amino-1-carbamimidoylpiperidine-4-carboxylic acid and 4-guanidinophenylalanine.

The large lipophilic R group may contain hetero atoms such as O, N, S or F but typically there is no more than one heteroatom, preferably it is nitrogen. This R group will preferably have no more than 2 polar groups, more preferably none or one, most preferably none.

In a particularly preferred embodiment the compounds, preferably peptides, are of formula (VI)

$AA_1$-$AA_2$-$AA_1$-$R_1$—$R_2$ (VI)

wherein:
$AA_1$ is a cationic amino acid, preferably lysine or arginine but may be histidine or any non-genetically coded or modified amino acid carrying a positive charge at pH 7.0;
$AA_2$ is an amino acid with a large lipophilic R group, the R group having 14-27 non-hydrogen atoms and preferably containing 2 or more, e.g. 2 or 3, cyclic groups which may be fused or connected, these cyclic groups will typically comprise 5 or 6 non-hydrogen atoms, preferably 6 non-hydrogen atoms; and
$R_1$ and $R_2$ are as defined above.

Further useful compounds include compounds of formulae (VII) and (VIII):

$AA_2$-$AA_1$-$AA_1$-$R_1$—$R_2$ (VII)

$AA_1$-$AA_1$-$AA_2$-$R_1$—$R_2$ (VIII)

wherein $AA_1$, $AA_2$, $R_1$ and $R_2$ are as defined above.

From amongst the above compounds certain are preferred. In particular, compounds wherein the amino acid with a large lipophilic R group, conveniently referred to herein as $AA_2$, is tributyl tryptophan (Tbt) or a biphenylalanine derivative such as Phe(4-(2'-Naphthyl)), Phe(4-(1'-Naphthyl)), Phe(4'-n-butylphenyl), Phe(4-4'-biphenyl) or Phe(4'-t-butylphenyl); Phe(4-(2'-Naphthyl)) and Tbt being most preferred.

A further preferred group of compounds are those in which —$R_1$—$R_2$ together is selected from the group —NHCH($CH_3$)$_2$, —NH($CH_2$)$_5$$CH_3$, —NH($CH_2$)$_3$$CH_3$, —NH($CH_2$)$_2$$CH_3$, —NHCH$_2$CH($CH_3$)$_2$, —NHcyclohexyl and —NHcyclopentyl, most preferred are compounds in which —$R_1$—$R_2$ is the group —NHCH($CH_3$)$_2$ or —NH($CH_2$)$_5$$CH_3$.

The compounds include all enantiomeric forms, both D and L amino acids and enantiomers resulting from chiral centers within the amino acid R groups and $R_2$.

Especially preferred compounds are the compounds in the table below, especially Compounds 1 and 2, wherein the compounds are of formula VI, VII or VIII, preferably formula VI, particularly of formula Arg-$AA_2$-Arg-$R_1$—$R_2$.

| Compound | $AA_2$ | $R_1R_2$ |
|---|---|---|
| 1 | 2,5,7-tri-tert-butyltryptophan | NHCH($CH_3$)$_2$ |
| 2 | 2,5,7-tri-tert-butyltryptophan | NH($CH_2$)$_5$$CH_3$ |
| 3 | 2,5,7-tri-tert-butyltryptophan | NH($CH_2$)$_3$$CH_3$ |
| 4 | 2,5,7-tri-tert-butyltryptophan | NH($CH_2$)$_2$$CH_3$ |
| 5 | 2,5,7-tri-tert-butyltryptophan | NH($CH_2$)$_{15}$$CH_3$ |
| 6 | 2,5,7-tri-tert-butyltryptophan | NHCH$_2$CH($CH_3$)$_2$ |
| 7 | 2,5,7-tri-tert-butyltryptophan | NHcyclohexyl |
| 8 | 2,5,7-tri-tert-butyltryptophan | NHcyclopentyl |
| 9 | Phe (4-4'-biphenyl) | NHCH($CH_3$)$_2$ |
| 10 | Phe (4-4'-biphenyl) | NH($CH_2$)$_5$$CH_3$ |
| 11 | Phe(4-(2'-Naphtyl)) | NHCH($CH_3$)$_2$ |
| 12 | Phe(4-(2'-Naphtyl)) | NH($CH_2$)$_5$$CH_3$ |

It is discussed in general terms above how the preferred motif of 3 amino acids, 2 cationic and 1 lipophilic, may be expanded or extended to longer peptides or peptidomimetics. The preferred compounds of formulae (I) to (VIII) may be expanded or extended in the manner described, especially to peptides of 4 or 5 amino acids and these represent a further preferred group of compounds for use according to the present invention.

A peptidomimetic is typically characterised by retaining the polarity, three dimensional size and functionality (bioactivity) of its peptide equivalent but wherein the peptide bonds have been replaced, often by more stable linkages. By 'stable' is meant more resistant to enzymatic degradation by hydrolytic enzymes. Generally, the bond which replaces the amide bond (amide bond surrogate) conserves many of the properties of the amide bond, e.g. conformation, steric bulk, electrostatic character, possibility for hydrogen bonding etc. Chapter 14 of "Drug Design and Development", Krogsgaard, Larsen, Liljefors and Madsen (Eds) 1996, Horwood Acad. Pub provides a general discussion of techniques for the design and synthesis of peptidomimetics. In the present case, where the molecule is reacting with a membrane rather than the specific active site of an enzyme, some of the problems described of exactly mimicking affinity and efficacy or substrate function are not relevant and a peptidomimetic can be readily prepared based on a given peptide structure or a motif of required functional groups. Suitable amide bond surrogates include the following groups: N-alkylation (Schmidt, R. et al., Int. J. Peptide Protein Res., 1995, 46, 47), retro-inverse amide (Chorev, M. and Goodman, M., Acc. Chem. Res, 1993, 26, 266), thioamide (Sherman D. B. and Spatola, A. F. J. Am. Chem. Soc., 1990, 112, 433), thioester, phosphonate, ketomethylene (Hoffman, R. V. and Kim, H. O. J. Org. Chem., 1995, 60, 5107), hydroxymethylene, fluorovinyl (Allmendinger, T. et al., Tetrahydron Lett., 1990, 31, 7297), vinyl, methyleneamino (Sasaki, Y and Abe, J. Chem. Pharm. Bull. 1997 45, 13), methylenethio (Spatola, A. F., Methods Neurosci, 1993, 13, 19), alkane (Lavielle, S. et. al., Int. J. Peptide Protein Res., 1993, 42, 270) and sulfonamido (Luisi, G. et al. Tetrahedron Lett. 1993, 34, 2391).

The peptidomimetic compounds of the present invention will typically have identifiable sub-units which are approximately equivalent in size and function to amino acids, preferably to cationic and lipophilic amino acids. The term 'amino acid' may thus conveniently be used herein to refer to the equivalent sub-unit of a peptidomimetic compound. Moreover, peptidomimetics may have groups equivalent to the R groups of amino acids and discussion herein of suitable R groups and of N and C terminal modifying groups applies, mutatis mutandis, to peptidomimetic compounds.

As is discussed in the text book referenced above, as well as replacement of amide bonds, peptidomimetics may involve the replacement of larger structural moieties with di- or tripeptidomimetic structures and in this case, mimetic moieties involving the peptide bond, such as azole-derived mimetics may be used as dipeptide replacements.

Peptidomimetics and thus peptidomimetic backbones wherein just the amide bonds have been replaced as discussed above are; however, preferred.

Suitable peptidomimetics include reduced peptides where the amide bond has been reduced to a methylene amine by treatment with a reducing agent e.g. borane or a hydride reagent such as lithium aluminium-hydride. Such a reduction has the added advantage of increasing the overall cationicity of the molecule.

Other peptidomimetics include peptoids formed, for example, by the stepwise synthesis of amide-functionalised polyglycines. Some peptidomimetic backbones will be readily available from their peptide precursors, such as peptides which have been permethylated, suitable methods are described by Ostresh, J. M. et al. in Proc. Natl. Acad. Sci. USA (1994) 91, 11138-11142. Strongly basic conditions will favour N-methylation over O-methylation and result in methylation of some or all of the nitrogen atoms in the peptide bonds and the N-terminal nitrogen.

Preferred peptidomimetic backbones include polyesters, polyamines and derivatives thereof as well as substituted alkanes and alkenes. The peptidomimetics will preferably have N and C termini which may be modified as discussed herein.

β and γ amino acids as well as a amino acids are included within the term 'amino acids', as are N-substituted glycines. The compounds of the invention include beta peptides and depsipeptides.

In the case of medical use, the peptides and peptide mimetics may be administered to the subject in any convenient form or by any convenient means, e.g. by topical, oral, parenteral, enteral, parenteral routes or by inhalation, topical, oral or parenteral routes are preferred.

The skilled man will be able to formulate the molecules of the invention into pharmaceutical compositions that are adapted for these routes of administration according to any of the conventional methods known in the art and widely described in the literature.

The active ingredient may be incorporated, optionally together with other active agents, with one or more conventional carriers, diluents and/or excipients, to produce conventional galenic preparations such as tablets, pills, powders (e.g. inhalable powders), lozenges, sachets, cachets, elixirs, suspensions, emulsions, solutions, syrups, aerosols (as a solid or in a liquid medium), ointments, soft and hard gelatine capsules, suppositories, sterile injectable solutions, sterile packaged powders, and the like. For application to oral, buccal and dental surfaces, toothpastes and mouthwashes are mentioned specifically.

Examples of suitable carriers, excipients, and diluents are lactose, dextrose, sucrose, sorbitol, mannitol, starches, gum acacia, calcium phosphate, inert alginates, tragacanth, gelatine, calcium silicate, microcrystalline cellulose, polyvinylpyrrolidone, cellulose, water syrup, water, water/ethanol, water/glycol, water/polyethylene, hypertonic salt water, glycol, propylene glycol, methyl cellulose, methylhydroxybenzoates, propyl hydroxybenzoates, talc, magnesium stearate, mineral oil or fatty substances such as hard fat or suitable mixtures thereof. Preferred excipients and diluents are mannitol and hypertonic salt water (saline).

The compositions may additionally include lubricating agents, wetting agents, emulsifying agents, suspending agents, preserving agents, sweetening agents, flavouring agents, and the like.

Parenterally administrable forms, e.g., intravenous solutions, should be sterile and free from physiologically unacceptable agents, and should have low osmolarity to minimize irritation or other adverse effects upon administration and thus solutions should preferably be isotonic or slightly hypertonic, e.g. hypertonic salt water (saline). Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405-1412 and 1461-1487 (1975) and The National Formulary XIV, 14th ed. Washington: American Pharmaceutical Association (1975). The solutions can contain preservatives, antimicrobial agents, buffers and antioxidants conventionally used for parenteral solutions, excipients and other additives which are compatible with the biopolymers and which will not interfere with the manufacture, storage or use of products.

For topical administration the peptide or peptide mimetic can be incorporated into creams, ointments, gels, transdermal patches and the like. The molecules can also be incorporated into medical dressings, for example wound dressings e.g. woven (e.g fabric) dressings or non-woven dressings (e.g. gels or dressings with a gel component).

Further topical systems that are envisaged to be suitable are in situ drug delivery systems, for example gels where solid, semi-solid, amorphous or liquid crystalline gel matrices are formed in situ and can conveniently be designed to control the release of the active agent from the matrix, e.g. release can be delayed and/or sustained over a chosen period of time. Such systems may form gels only upon contact with biological tissues or fluids. Typically the gels are bioadhesive.

In the case of biofilms on an inanimate surface, the peptide or mimetic may be applied to the surface to be treated in any convenient composition or formulation, or by any convenient means. E.g. in liquid, gel, gel-sol, semi-solid or solid form (e.g. solutions, suspensions, homogenates, emulsions, pastes, powders, aerosols, vapours). Typically the compositions for treating such inanimate surface biofilms will be a non-pharmaceutically acceptable composition. The choice of composition form will be dictated by the biofilm structure and colony composition and location. For instance, if the location of the biofilm is a fluid line it might be convenient to apply a fluid composition. The skilled person is readily able to prepare suitable compositions from his common general knowledge.

In medical applications, the peptide or mimetic may conveniently be administered at concentrations of 5-500 mg/l, preferably 20-100 mg/l, e.g. 40-60 mg/l.

The invention will now be further described with reference to the following non-limiting Examples and Figures, in which:

FIG. 2 shows biomass quantification with Crystal Violet (CV) (top panel) and quantification of metabolic activity with Alamar blue (AB)(bottom panel) in a 24 h old biofilm of 6 different staphylococcal strains. A clear correlation between CV and AB can be seen.

FIG. 3 (A-D) are graphs showing the effect of 24 h treatment with rifampicin (A), linezolid (B), tetracycline (C) and vancomycin (D) on 24 h old biofilm of 6 different staphylococcal strains. For each strain, bars represent from left to right: negative control, positive control, treatment with antibiotic (vancomycin, linezold, tetracycline) concentration 5 mg/L, 50 mg/L, and 500 mg/L. For rifampicin, the concentrations were 0.01 mg/L, 0.1 mg/L and 1 mg/L. Values are means of three experiments±SD. * means strong suppression of metabolic activity. ** means complete suppression of metabolic activity.

Figure 4:
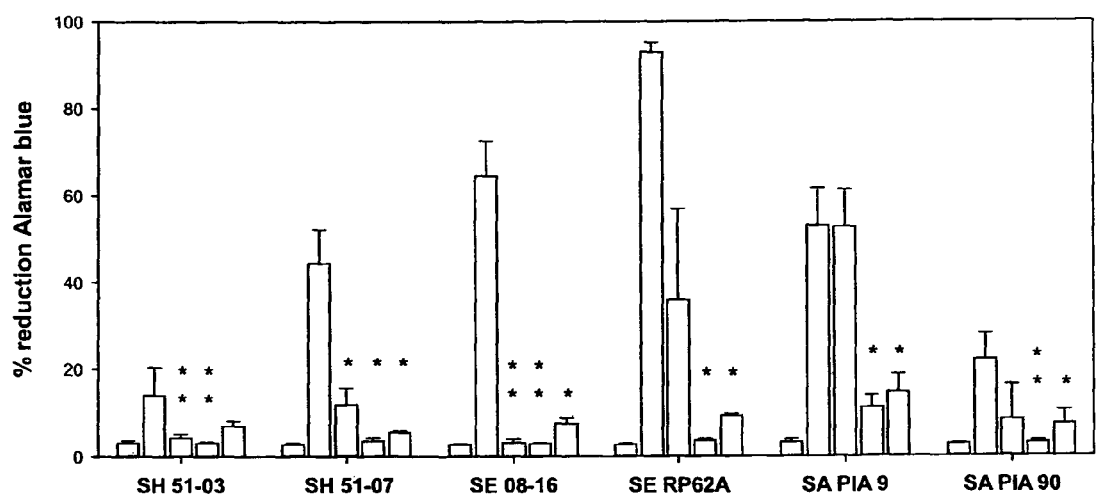

FIG. 4 (A-C) are graphs showing the effect of 24 h treatment with 3 different SAMPs (compounds A, B and C respectively) on 24 h old biofilm of 6 different staphylococcal strains. For each strain, bars represent from left to right negative control, positive control, treatment with SAMPs in concentration 5 mg/L, 50 mg/L, and 500 mg/L. Values are means of three experiments±SD. * means strong suppression of metabolic activity. ** means complete suppression of metabolic activity.

FIG. 5 are photos showing 48 h old *S. haemolyticus* 51-07 biofilm grown on cover slide discs. The biofilms were stained with LIVE/DEAD staining and investigated with confocal laser scanning microscopy. Untreated biofilm (A); biofilm treated for 24 h with vancomycin 50 mg/L (B); vancomycin 500 mg/L (C); tetracycline 50 mg/L (D); tetracycline 500 mg/L (E); Compound 150 mg/L (F) and Compound 1500 mg/L (G).

Figure 6:
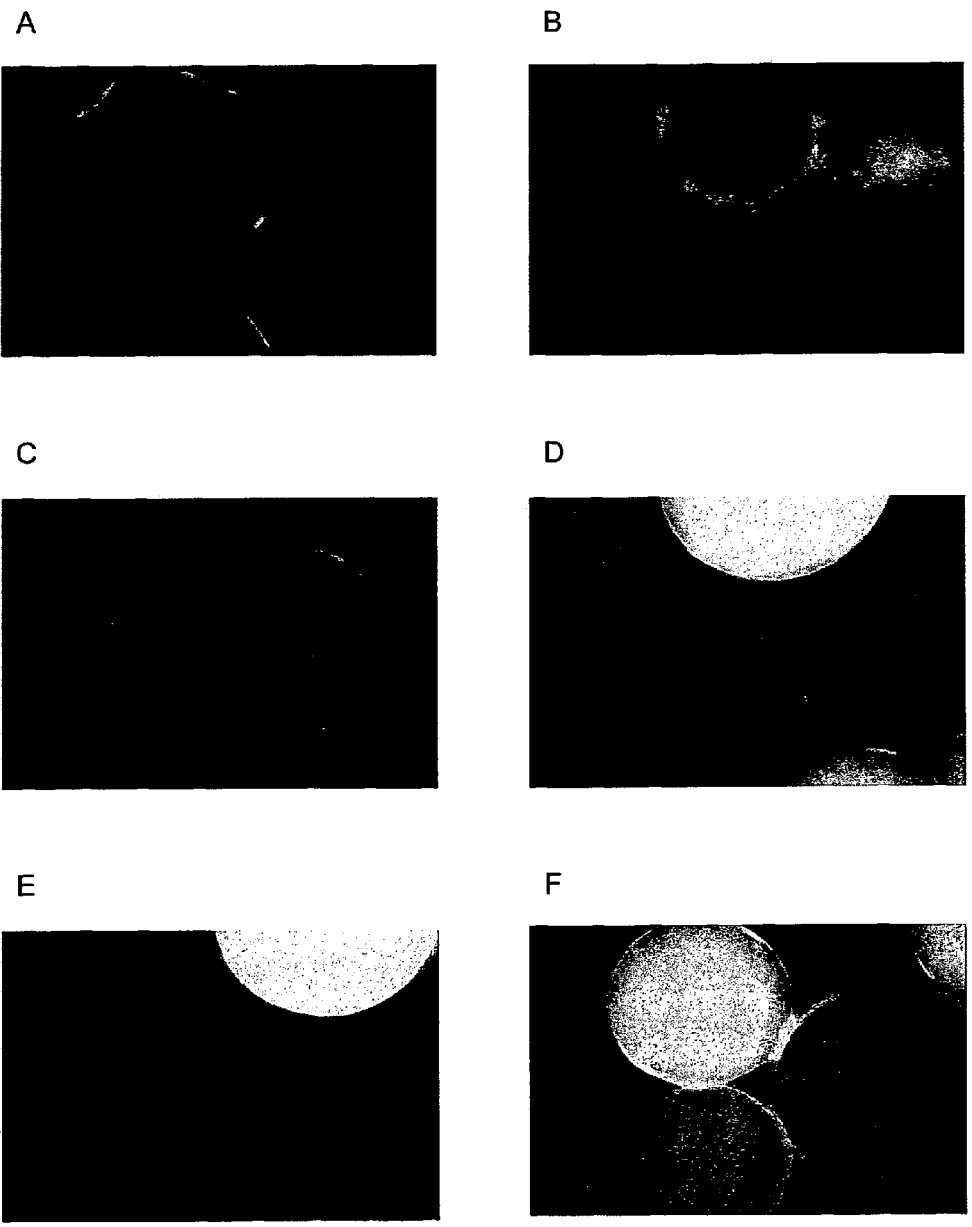

FIG. 6 is a photomicrograph of A) An uncoated aminomethylated polystyrene HL particle, B) An uncoated aminomethylated polystyrene HL particle after 24 h incubation with *Staphylococcus epidermidis*, C) Argininyl-(2,5,7-tri-tert-butyl)tryptophanyl-argininyl-polystyrene particle after 24 h incubation with *Staphylococcus epidermidis*, D) Argininyl-(2,5,7-tri-tert-butyl)tryptophanyl-argininyl-aminohexanoyl-polystyrene particle after 24 h incubation with *Staphylococcus epidermidis*, E) Argininyl-(2,5,7-tri-tert-butyl) tryptophanyl-argininyl-phenylalaninyl-polystyrene particle after 24 h incubation with *Staphylococcus epidermidis*, F) Argininyl-(2,5,7-tri-tert-butyl)tryptophanyl-argininyl-phenylalaninyl-aminohexanoyl-polystyrene particle after 24 h incubation with *Staphylococcus epidermidis*.

EXAMPLE 1

Material and Methods

Peptide Synthesis
Chemicals

Protected amino acids Boc-Arg-OH, and Boc-4-phenyl-Phe were purchased from Bachem AG while Boc-4-iodophenylalanine was purchased from Aldrich. isopropylamine, propylamine, hexylamine, butylamine, hexadecylamine, isobutylamine, cyclohexylamine and cyclopentylamine making up the C-terminal of the peptide were purchased from Fluka. Diisopropylethylamine (DIPEA), 1-hydroxybenzotriazole (1-HOBt), chlorotripyrrolidinophosphonium hexafluorophosphate (PyCloP) and O-(benzotriazol-1-yl)-N,N,N',N' tetramethyluronium hexafluorophosphate (HBTU) were purchased from Fluka. 4-n-Butylphenylboronic acid, 4-t-butylphenylboronic acid, 4-biphenylboronic acid, 2-naphthylboronic acid, tri ortho-tolylphosphine, benzylbromide and palladium acetate were purchased from Aldrich. Solvents were purchased from Merck, Riedel-de Haën or Aldrich.

Preparation of Amino Acids

Preparation of Boc-2,5,7-tri-tert-butyltryptophan-OH

A mixture of H$_2$N-Trp-OH (1.8 g, 8.8 mmol), t-BuOH (4.7 g, 63.4 mmol) in trifluoroacetic acid (19 mL) is stirred at 70° C. for 3 hours. The volume of the resulting mid-brown translucent solution is reduced on a rotary evaporator at room temperature for 30 min and then triturated by means of adding 60 mL of 7% (by weight) NaHCO3 drop-wise. The gray/white granular solid obtained is then recovered by vacuum filtration and dried in vacuo at room temperature for 24 hours. The product is isolated by crystallization from a near boiling mixture of 40% ethanol in water. Volumes typically are approximately 20 mL per gram of crude product.

A first crystallization from crude produces isolated product of 80-83% purity (HPLC) with respect to all other substances in the sample and approximately 94-95% purity with respect to the known TBT analogues. Yields at this stage are in the range 60-65%.

Benzylation of Boc-4-iodophenylalanine

Boc-4-iodophenylalanine (1 equivalent) was dissolved in 90% methanol in water and neutralized by addition of cesium carbonate until a weak alkaline pH (determined by litmus paper). The solvent was removed by rotary evaporation, and remaining water in the cesium salt of Boc-4-iodophenylalanine was further reduced by repeated azeotropic distillation with toluene. The resulting dry salt was dissolved in dimethylformamide (DMF), benzylbromide (1.2 equivalents) was added and the resulting mixture was stirred for 6-8 h. At the end of the reaction DMF was removed under reduced pressure and an oil containing the title compound is formed. This oil was dissolved in ethyl acetate and the resulting solution was washed with equal volumes of citric acid solution (three times), sodium bicarbonate solution and brine. The title compound was isolated as a pale yellow oil in 85% yield by flash chromatography using dichloromethane:ethyl acetate (95:5) as eluent. Crystalline benzyl Boc-4-iodophenylalanine could be obtained by recrystallisation from n-heptane.

General Procedure for Suzuki Couplings

Benzyl Boc-4-iodophenylalanine (1 equivalent), arylboronic acid (1.5 equivalents), sodium carbonate (2 equivalents), palladium acetate (0.05 equivalent) and tri ortho-tolylphosphine (0.1 equivalent) was added to a degassed mixture of dimethoxyethane (6 ml/mmol benzyl Boc-4-iodophenylalanine) and water (1 ml/mmol benzyl Boc-4-iodophenylalanine). The reaction mixture was kept under argon and heated to 80° C. for 4-6 h. After cooling to room temperature the mixture is filtered through a short pad of silicagel and sodium carbonate. The filter cake was further washed with ethyl acetate. The filtrates were combined and the solvents were removed under reduced pressure. The products were isolated by flash chromatography using mixtures of ethyl acetate and n-hexane as eluent.

Preparation of Boc-Phe(4-4'-biphenyl)-OBn

The title compound was prepared in 61% yield from 4-biphenylboronic acid using the general procedure for Suzuki couplings. Boc-Phe(4-4'-biphenyl)-OBn was isolated by recrystallisation of the crude product from n-heptane.

Preparation of Boc-Phe(4-(2'-Naphtyl))-OBn

The title compound was prepared in 68% yield from 2-naphthylboronic acid using the general procedure for Suzuki couplings. Boc-Phe(4-(2'-Naphtyl))-OBn was isolated by recrystallisation of the crude product from n-heptane.

General Procedure for Deesterification of Benzyl Esters

The Benzyl ester is dissolved in DMF and hydrogenated for 2 days at ambient pressure using 10% Pd on carbon as catalyst. At the end of the reaction the catalyst is removed by filtration and the solvent is removed under reduced pressure. The free acids are isolated by recrystallisation from diethyl ether.

Preparation of Boc-Phe(4-4'-biphenyl)-OH

The title compound was prepared in 61% yield from Boc-Phe(4-4'-biphenyl)-OBn using the general procedure for deesterification.

Preparation of Boc-Phe(4-(2'-Naphtyl))-OH

The title compound was prepared in 68% yield from Boc-Phe(4-(2'-Naphtyl))-OBn using, the general procedure for deesterification.

General Procedure for Solution Phase Peptide Synthesis Using HBTU

The peptides were prepared in solution by stepwise amino acid coupling using Boc protecting strategy according to the following general procedure. The C-terminal peptide part with a free amino group (1 eq) and the Boc protected amino acid (1.05 eq) and 1-hydroxybenzotriazole (1-HOBt) (1.8 eq) were dissolved in DMF (2-4 ml/mmol amino component) before addition of diisopropylethylamine (DIPEA) (4.8 eq). The mixture was cooled on ice and O-(benzotriazol-1-yl)-N,N,N',N' tetramethyluronium hexafluorophosphate (HBTU) (1.2 eq) was added. The reaction mixture was shaken at ambient temperature for 1-2 h. The reaction mixture was diluted by ethyl acetate and washed with citric acid, sodium bicarbonate and brine. The solvent was removed under vacuum and the Boc protecting group of the resulting peptide was deprotected in the dark using 95% TFA or acetylchloride in anhydrous methanol.

Solution phase amide formation using PyCloP. Synthesis of Boc-Arg-N($CH_2$Ph)$_2$. A solution of Boc-Arg-OH (1 eq), NH($CH_2$Ph)$_2$ (1.1 eq) and PyCloP (1 eq) in dry DCM (filtered through alumina)(2 ml) and DMF (1 ml). The solution was cooled on ice and DIPEA (2 eq) was added under stirring. The solution was stirred for 1 h at room temperature. The reaction mixture was evaporated, and redissolved in ethyl acetate and washed with citric acid, sodium bicarbonate and brine. The solvent was removed under vacuum and the Boc protecting group of the resulting peptide was deprotected in the dark using 95% TFA.

Peptide Purification and Analysis

The peptides were purified using reversed phase HPLC on a Delta-Pak (Waters) $C_{18}$ column (100 Å, 15 μm, 25×100 mm) with a mixture of water and acetonitrile (both containing 0.1% TFA) as eluent. The peptides were analyzed by RP-HPLC using an analytical Delta-Pak (Waters) $C_{18}$ column (100 Å, 5 μm, 3.9×150 mm) and positive ion electrospray mass spectrometry on a VG Quattro quadrupole mass spectrometer (VG Instruments Inc., Altringham, UK).

Bacterial Strains and Growth Conditions

The six staphylococcal strains (2 *S. epidermidis*, 2 *S. haemolyticus* and 2 *S. aureus*) used in this study were selected based on their previously known biofilm forming capacity (Table 1).

Bacteria were grown overnight at 37° C. in cation adjusted Mueller-Hinton II Broth (MHIIB).

TABLE 1

Bacterial strains used in this study; susceptibility to antibiotics and SAMPs, and biofilm profile.

| Strain | Source | MIC antibiotics (mg/L) | | | | | | MIC SAMPs (mg/L) | | | Biofilm | |
| | | RIF | VAN | TET | LZD | GEN | OXA | Compound A | Compound B | Compound C | Ica[d] | optical density |
| --- | --- | --- | --- | --- | --- | --- | --- | --- | --- | --- | --- | --- |
| SH[a] TUH 51-03 | Blood culture | <0.016 | 4 | 1 | 0.5 | 64 | >256 | 8 | 4 | 4 | + | 0.37 |
| SH TUH 51-07 | Blood culture | 0.016 | 2 | 0.5 | 0.5 | 64 | >256 | 8 | 4 | 4 | + | 0.77 |
| SE[b] TUH 08-16 | Blood culture | 0.016 | 2 | 2 | 2 | 256 | 16 | 4 | 2 | 2 | + | 0.63 |
| SE RP62A ATCC 35984 | Blood culture | <0.016 | 4 | 0.5 | 1 | 8 | 8 | 8 | 4 | 4 | + | 1.33 |
| SA[c] PIA 9 | Joint fluid | <0.016 | 2 | 0.5 | 2 | 1 | 1 | 8 | 2 | 4 | + | 3.20 |
| SA PIA90 | Joint fluid | 0.016 | 2 | 0.5 | 1 | 0.5 | 1 | 8 | 2 | 2 | + | 0.40 |

[a]SH; *Staphylococcus haemolyticus*
[b]SE; *Staphylococcus epidermidis*
[c]SA; *Staphylococcus aureus*
[d]ica; PCR detection of icaD as a marker of the operon

Figure 1:
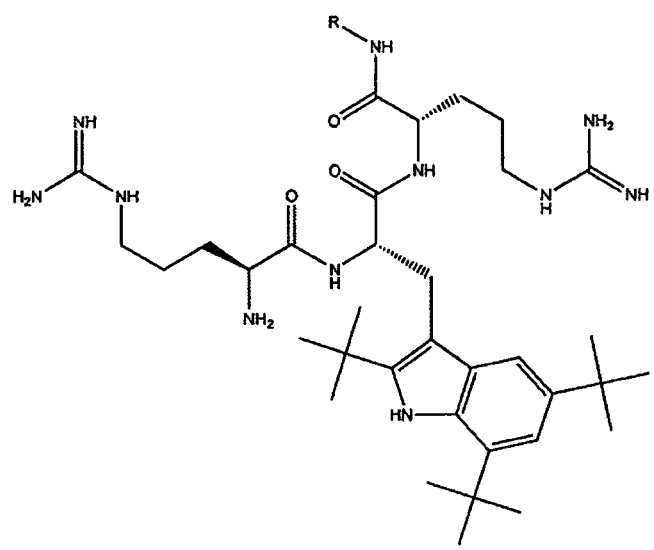
FIG. 1 shows the Chemical structure of the SAMPs used in this study. Structure 1 is the structure of Compound A: where R=iPr, Compound B: where R=(CH$_2$)$_2$Ph and Compound C: where R=n-C$_6$H$_{13}$.

Antibiotics, SAMPs and Susceptibility Testing Under Planktonic Growth Condition We determined the MICs of oxacillin, gentamicin, tetracycline, vancomycin and linezolid using E-test (AB Biodisk, Solna, Sweden) and MICs of rifampicin using broth microdilution assay. Breakpoints were interpreted according to EUCAST criteria. We selected 3 different SAMPs (Compounds A, B and C; Lytix Biopharma, Tromsø, Norway—see FIG. 1) based on previously known antimicrobial activities, and determined their exact MICs with broth microdilution assay. All 3 SAMPs are tripeptides with two arginine residues providing their cationic moieties (FIG. 1). The lipophilic bulk is provided by a modified tryptophane derivate. The difference between the compounds is the size of the C-terminal modification; Compound A has the smallest and Compound B has the largest C-terminal modification (FIG. 1). The molecular weights of the SAMPs are in the range of 700-800 Dalton.

Biofilm Formation and Quantification of Activity Against Biofilms

Biofilm formation was induced in 96-well flat bottom microtitre plates (Nunclon Surface, NUNC, Roskilde, Denmark). First, overnight cultures were diluted 1:100 in MHIIB (*S. epidermidis* and *S. haemolyticus*) or tryptic soy broth (TSB) with 5% glucose and 5% NaCl (*S. aureus*). Two hundred of this bacterial suspension ($10^7$ cfu/ml) was added to each well and incubated for 24 h at 37° C. After 24 h the wells were carefully washed twice with phosphate-buffered saline (PBS) to remove planktonic bacteria. The washing procedure was evaluated by measuring metabolic activity of the PBS with the Alamar blue method, described in detail below. DNA extractions and PCRs for icaD, as a marker for the ica operon, were carried out as previously reported (de Silva et al., J. Clin. Microbiol. [2002] 40: 382-388).

The washed biofilms were subjected to treatment with antibiotics or SAMPs at different concentrations. Stock solutions of the tetracycline (Sigma Aldrich), vancomycin (Alpharma) and linezolid (Pfizer) were diluted in MHIIB to 5 mg/L, 50 mg/L and 500 mg/L, and rifampicin (Sigma Aldrich) was diluted in MHIIB to 0.01 mg/L, 0.1 mg/L and 1 mg/L. Trifluoroacetate salts of the SAMPs were dissolved in sterile water and diluted to 5 mg/L, 50 mg/L and 500 mg/L in MHIIB. 200 µl of antibiotics or SAMPs, in different concentrations, were added to each well and incubated for 24 h at 37° C. Positive controls were untreated biofilms only added 200 µl MHIIB. Negative controls were only 200 µl MHIIB, with no bacteria added.

We quantified the metabolic activity of biofilm with a slightly modified method previously described by Pettit et al. in *Antimicrob. Agents Chemother.* 2005; 49:2612-7. Briefly, the wells were washed twice with PBS. We then added 250 µl MHIIB with 5% Alamar blue (AB; Invitrogen, Carlsbad, Calif., USA) to each well. AB is a redox indicator which both fluoresces and changes colour in response to chemical reduction. The extent of reduction is a reflection of bacterial cell viability. After 1 h incubation at 37° C., absorbance was recorded at 570 and 600 nm using Versamax tuneable microplate reader (Molecular Devices, Sunnyvale, Calif., USA). All assays were performed 3 times with 8 parallels. The highest and lowest value of each run was excluded from the analyses, and the remaining 18 values were averaged.

The biofilm method quantifying metabolic activity was compared to a standard semiquantitative biomass-quantification method in 96-well microtitre plates. For these experiments we grew 24 h biofilms of all 6 staphylococcal strains and analyzed metabolic activity with AB, as described above. Biomass quantification on the 24 h biofilms was performed by staining the biofilm with crystal violet (CV). After staining, ethanol:acetone (70:30) was added to each well to dissolve remaining crystal violet along the walls of the wells. The optical density (OD) was then recorded at 570 nm using a spectrophotometer.

Biofilm Imaging

One ml aliquots of MHIIB-diluted overnight culture was used to grow *S. haemolyticus* TUH 51-07 biofilm on plastic coverslides (Thermanox, cellculture treated on one side, NUNC, Roskilde, Denmark) in 24-well dishes (Falcon 3047, Becton Dickinson, NJ, USA) for 24 h. The coverslides were then washed carefully with PBS, moved to a new plate and treated for 24 h with tetracycline 50 mg/L and 500 mg/L, vancomycin 50 mg/L and 500 mg/L, or Compound A 50 mg/L and 500 mg/L. The coverslides were washed again with 9% NaCl and stained with a LIVE/DEAD kit (Invitrogen Molecular Probes, Eugene, Oreg., USA) following the manufacturer's instructions. This stain contains SYTO 9 (green fluorescent) and propidium iodide (PI; red fluorescent), both binding to DNA. When used alone, the SYTO 9 generally stains all bacteria in a population; both those with intact and those with damaged membranes. In contrast, PI penetrates only bacteria with damaged membranes, causing a reduction in the SYTO 9 stain green fluorescence when both dyes are present. We examined treated and untreated biofilms with a Leica TCS SP5 (Leica Microsystems CMS Gmbh, Mannheim, Germany) confocal laser scanning microscope (CLSM). Images were obtained using a 63×1.2 NA HCX PL APO water immersion lens. For detection of SYTO9 (green channel), we used the 488 nm line of the argon laser and a detection bandwidth of 495-515 nm. For PI detection (red channel), we used the 561 nm line and a detection bandwidth of 615-660 nm. The two fluorescent-signals were collected sequentially at 400 Hz. Image analyses and export was performed in Leica LAS AF version 1.8.2.

Statistical Analysis and Evaluations

The percent reduction of AB was calculated according to the manufacturer's formula (Invitrogen, Carlsbad, USA). We calculated mean and standard deviations (SD) of all repeated measurements. Pearson's two-tailed correlation between the AB method and the CV method (FIG. 2) was calculated on averaged data from all 6 staphylococcal strains. Statistical analysis was performed with SPSS for Windows software version 14.0.

We present the crude percentage values of AB reduction, including positive and negative control (FIGS. 3 and 4). We defined two levels of antimicrobial suppression of metabolic activity. A strong suppression was obtained if an agent, after adjusting for the negative control, at a certain concentration caused 75% reduction of AB compared to positive control. A complete suppression was obtained if an agent at a certain concentration caused a reduction of AB negative control value+2SD.

Results

Table 1 above summarizes MICs of the antibiotics and SAMPs. All 6 strains were susceptible to vancomycin, linezolid, rifampicin, vancomycin and tetracycline. The two *S. aureus* strains were susceptible to gentamicin and oxacillin, while the four other staphylococcal strains were resistant to these agents. MICs for the SAMPs were in general higher than MICs for the antibiotics.

There was a strong correlation (R 0.939, p=0.002) between biomass quantified by CV staining and biofilm metabolic activity quantified by AB reduction in the 24 h old biofilm (FIG. 2). There was a negligible metabolic activity in the PBS after the washing, indicating almost complete removal of planktonic bacteria from the wells (data not shown).

FIGS. 3 and 4 show the percentage of AB reduction in untreated and treated biofilm. With few exceptions, the tested antibiotics reduced metabolic activity of all strains at concentrations around MIC. With higher antibiotic concentrations, roughly 10-20×MIC, all antibiotics caused a strong suppression of metabolic activity, except in S. aureus PIA9. However, only tetracycline was able to cause a complete suppression of metabolic activity in one strain (S. aureus PIA 90). None of the antibiotics caused 50% AB reduction in S. aureus PIA9 biofilm. This strain seemed to create a biofilm completely resistant to vancomycin.

Compounds A, B and C caused a strong or complete suppression of metabolic activity in all biofilms at concentrations of 50 mg/L, except in S. aureus PIA 9. In some strains even a concentration of 5 mg/L was sufficient to cause complete suppression.

FIG. 5 shows confocal microscopy pictures of a S. haemolyticus TUH 51-07 biofilm using LIVE/DEAD staining. As expected, the untreated biofilm showed green cells with intact cell membranes. In the biofilm subjected to treatment with Compound A in a concentration of 50 mg/L and especially 500 mg/L almost all cells are stained red, indicating dead bacteria. In biofilm subjected to treatment with 500 mg/L tetracycline a significant part of the cells are still green indicating live bacteria with intact cell membrane. Treatment of the biofilm with vancomycin (FIG. 5d) at a concentration around the peak values obtained in clinical practice (50 mg/L) showed predominantly green cells (live organisms).

All of the tested SAMPs were clearly more effective in reducing metabolic activity in staphylococcal biofilms at low concentrations compared to antibiotics, even though they generally had higher MICs under planktonic growth conditions. Under planktonic growth conditions all strains used in this study were sensitive to vancomycin, linezolid, rifampicin and tetracycline. Poor antimicrobial activity of vancomycin on staphylococcal biofilms has previously been reported. In our study, vancomycin at 50 mg/L exerted a strong suppression of metabolic activity on mature biofilms from 4 out of the 6 strains tested. Still, CLSM confirmed that most bacteria were not killed by this concentration. In general, antibiotics were rarely able to cause a complete suppression of metabolic activity. In contrast, SAMPs were frequently able to suppress metabolic activity completely, indicating effective killing. Images obtained by the CLSM further supported this finding. Treatment with 500 mg/L of Compound A caused membrane damage of all cells, indicating cell lysis in the S. haemolyticus biofilm. Biofilms treated with 500 mg/L tetracycline still contained a significant number of living cells, as recorded by LIVE/DEAD staining, even though there was hardly any measurable metabolic activity in the corresponding biofilm assay.

EXAMPLE 2

Peptidic Surface Modification of Polystyrene Particles

Preparation of Coated Particles

1.
To a 20 mL peptide reactor was added 560 mg (0.5 mmole) of aminomethylated polystyrene HL particles (100-200 mesh, 0.90 mmole/g substitution) which were then washed 2×10 min with 8 mL DCM. A further 8 mL of DCM was then added and the particles permitted to swell for 1 hour before the reactor was drained prior to the first coupling.

2.
To 8 mL of DMF was added 3 equivalents of Boc amino-acid and 683 mg (3.6 equivalents) of O-(Benzotriazol-1-yl)-N,N,N',N'-tetramethyluronium (HBTU) coupling reagent. Immediately prior to transfer of the mixture to the reactor 0.855 mL (10 equivalents) of N-Ethyldiisopropylamine (DI-PEA) was added and the mixture transferred to the reaction in one portion. The reactor was then agitated moderately whilst the reaction was permitted to run overnight at room temperature.

3
The particles were then washed 3×15 min with 8 mL DMF and 2×10 min with 8 mL DCM.

4.
At this point a small sample was removed from the reactor and subjected to the Kaiser test in order to determine whether there was any remaining uncoupled amine.

5.
If the Kaiser test gives a positive result the procedure was repeated from and including point 2 with the same amino acid. In the event that the test was negative (no uncoupled amine remaining) 8 mL of TFA/DCM (1:1) was added to the reactor to remove the Boc group from the newly coupled amino acid and the reactor agitated moderately for 1 hour.

6.
The particles were then washed 3×15 min with 8 mL DCM and 2×10 min with 8 mL DMF.

7.
The procedure was now repeated from and including point 2 to and including point 6 with the next amino acid to be coupled.

8.
When the final amino acid unit has completed stage 5 in the procedure outlined above the particles were washed 4×15 min with 8 mL DCM and dried in the reactor under nitrogen flow for 30 min before being dried under vacuum at room temperature for 24 hours. The particles were then stored in sealed vials at 4° C.

In the manner described above, the following peptide coated particles were prepared in close to quantitative yields using the appropriate amino acids:

Argininyl-(2,5,7-tri-tert-butyl)tryptophanyl-argininyl-polystyrene (peptide according to the invention)

Argininyl-(2,5,7-tri-tert-butyl)tryptophanyl-argininyl-aminohexanoyl-polystyrene (peptide according to the invention)

Argininyl-(2,5,7-tri-tert-butyl)tryptophanyl-argininyl-phenylalaninyl-polystyrene (peptide according to the invention)

Argininyl-(2,5,7-tri-tert-butyl)tryptophanyl-argininyl-phenylalaninyl-aminohexanoyl-polystyrene (peptide according to the invention)

Reduced Bacterial Colonization of Surface Coated Particles

The particles prepared above were incubated with Staphylococcus epidermidis for 24 h. The amount of bacterial colonization on the bacterial surface was determined by fluorescence microscopy (excitation frequency of 485 nm, emission frequency 498 nm) after staining of the biofilm forming bacteria by Syto9 according to standard procedures.

The effect on colonization was determined by visual inspection of photomicrographs of the polystyrene particles. FIG. 6 shows the photomicrograph of:

A) An uncoated aminomethylated polystyrene HL particle
B) An uncoated aminomethylated polystyrene HL particle after 24 h incubation with *Staphylococcus epidermidis*
C) Argininyl-(2,5,7-tri-tert-butyl)tryptophanyl-argininyl-polystyrene particle after 24 h incubation with *Staphylococcus epidermidis*
D) Argininyl-(2,5,7-tri-tert-butyl)tryptophanyl-argininyl-aminohexanoyl-polystyrene particle after 24 h incubation with *Staphylococcus epidermidis*.
E) Argininyl-(2,5,7-tri-tert-butyl)tryptophanyl-argininyl-phenylalaninyl-polystyrene particle after 24 h incubation with *Staphylococcus epidermidis*
F) Argininyl-(2,5,7-tri-tert-butyl)tryptophanyl-argininyl-phenylalaninyl-aminohexanoyl-polystyrene particle after 24 h incubation with *Staphylococcus epidermidis*

The biofilm colonization of the polystyrene particle in Figure B) can readily be observed by the Fluffy, furry nature of the surface of the particle compared to the smooth surface of the polystyrene particle in Figure A). Figures C), D), E) and F) show the effect of the four peptide coatings on the colonization by *Staphylococcus epidermidis*. Coating with Argininyl-(2,5,7-tri-tert-butyl) tryptophanyl-argininyl (Figure C)), Argininyl-(2,5,7-tri-tert-butyl)tryptophanyl-argininyl aminohexanoyl (Figure D), Argininyl-(2,5,7-tri-tert-butyl)tryptophanyl-argininyl-phenylalaninyl (Figure E)) and Argininyl-(2,5,7-tri-tert-butyl)tryptophanyl-argininylphenylalaninyl-aminohexanoyl (Figure F)) are each shown to be effective in preventing biofilm formation by hindering bacterial colonization.

EXAMPLE 3

Biofilm Formation and Quantification of Activity Against Biofilms

Biofilm formation was induced in 96-well flat bottom microtitre plates (Nunclon Surface, NUNC). First, overnight cultures were diluted 1:100 in MHIIB (*S. epidermidis* and *S. haemolyticus*) or tryptic soy broth (TSB) with 5% glucose and 5% NaCl (*S. aureus*). 200 ml of this bacterial suspension (107 cfu/ml) was added to each well and incubated for 24 h at 37° C. After 24 h the wells were carefully washed twice with phosphate-buffered saline (PBS) to remove planktonic bacteria. The washing procedure was carefully evaluated by measuring metabolic activity of the PBS with the Alamar blue method, described in detail below.

The washed biofilms were subjected to treatment with the Compounds at different concentrations.

Trifluoroacetate salts of the compounds were dissolved in sterile water and diluted to 5 mg/L, 50 mg/L and 500 mg/L in MHIIB. 200 pa of the Compounds, in different concentrations, were added to each well and incubated for 24 h at 37° C. Positive controls were untreated biofilms only added 200 MHIIB. Negative controls were only 200 μl MHIIB, with no bacteria added.

The metabolic activity of the biofilm was quantified with a slightly modified method previously described by Pettit et al. Antimicrob. Agents Chemother. 2005; 49: 2612-7. Briefly, after the 24 h incubation with antimicrobial agents the wells were again washed twice with PBS and then added 250 ml MHIIB with 5% Alamar blue (AB; Biosource, Camarillo, Calif., USA). AB is a redox indicator which both fluoresces and changes colour in response to chemical reduction. The extent of reduction is a reflection of bacterial cell viability. After 1 h incubation at 37° C., absorbance was recorded at 570 and 600 nm using Versamax tuneable microplate reader (Molecular Devices, Sunnyvale, Calif., USA). All assays were performed 3 times with 8 parallels. The highest and lowest value of each run was excluded from the analyses, and the remaining 18 values were averaged.

Peptide Sequences

| Peptide | Sequence |
|---------|----------|
| ME 143  | R-Phe(4-(2'-naphthyl)-R-NH-CH(CH3)2 |
| ME 171 B | R-W-W-R-NH-CH2CH2Ph (SEQ ID NO: 1) |
| ME 172  | W-R-W-W-R-NH-CH2CH2Ph (SEQ ID NO: 2) |

Minimum Inhibitory Concentration (MIC) on Planctonic Bacteria

| MIC | ME 172 | ME 143 | ME 171 B |
|-----|--------|--------|----------|
| 8-16 *S. epidermidis* | 16 μg/ml | 32 μg/ml | 64 μg/ml |
| 42-77 *S. epidermidis* | 16 μg/ml | 32 μg/ml | 64 μg/ml |
| 51-03 *S. haemolyticus* | 8 μg/ml | 16 μg/ml | 32 μg/ml |
| 51-07 *S. haemolyticus* | 8 μg/ml | 16 μg/ml | 32 μg/ml |
| PIA 9 *S. aureus* | 16 μg/ml | 64 μg/ml | 128 μg/ml |
| PIA 90 *S. aureus* | 32 μg/ml | 64 μg/ml | 128 μg/ml |

Minimum Biofilm Inhibitory Concentration (MBIC) for ME 172 Measured as Survival Rate (%)

| MIC | 5 μg/ml | 50 μg/ml | 500 μg/ml |
|-----|---------|----------|-----------|
| 8-16 *S. epidermidis* | 100 | 80 | 20 |
| 42-77 *S. epidermidis* | 100 | 85 | 10 |
| 51-03 *S. haemolyticus* | 100 | 6 | 8 |
| 51-07 *S. haemolyticus* | 100 | 41 | 12 |
| PIA 9 *S. aureus* | 100 | 100 | 18 |
| PIA 90 *S. aureus* | 100 | 55 | 10 |

Minimum Biofilm Inhibitory Concentration (MBIC) for ME 143 Measured as Survival Rate (%)

| MIC | 5 μg/ml | 50 μg/ml | 500 μg/ml |
|-----|---------|----------|-----------|
| 8-16 *S. epidermidis* | 100 | 75 | 6 |
| 42-77 *S. epidermidis* | 100 | 80 | 12 |
| 51-03 *S. haemolyticus* | 100 | 20 | 9 |
| 51-07 *S. haemolyticus* | 100 | 12 | 8 |
| PIA 9 *S. aureus* | 100 | 100 | 14 |
| PIA 90 *S. aureus* | 100 | 80 | 7 |

Minimum Biofilm Inhibitory Concentration (MBIC) for ME 171B Measured as Survival Rate (%)

| MIC | 5 μg/ml | 50 μg/ml | 500 μg/ml |
|-----|---------|----------|-----------|
| 8-16 *S. epidermidis* | 100 | 70 | 4 |
| 42-77 *S. epidermidis* | 100 | 90 | 10 |
| 51-03 *S. haemolyticus* | 100 | 8 | 9 |
| 51-07 *S. haemolyticus* | 100 | 60 | 12 |
| PIA 9 *S. aureus* | 100 | 100 | 90 |
| PIA 90 *S. aureus* | 100 | 80 | 5 |

The above data shows that peptides of 3 to 5 residues in length are effective against biofilms even though their intrinsic activity against planktonic bacteria are modest.

The invention claimed is:

1. A solid support having covalently attached thereto through a cycloaddition reaction a peptide or peptidomimetic, wherein said peptide or peptidomimetic
   a) carries a net positive charge;
   b) is 2 to 6 amino acids in length or is an equivalently sized peptidomimetic; and
   c) is amphipathic in nature, having one or more lipophilic groups, one of said lipophilic groups comprising at least 7 non-hydrogen atoms.

2. The solid support as claimed in claim 1 wherein said peptide or peptidomimetic has a net charge of at least plus 2.

3. The solid support as claimed in claim 1 wherein said peptide is 3 amino acids in length or said peptidomimetic is equivalently sized.

4. The solid support as claimed in claim 1 wherein said lipophilic group has 9 to 12 non-hydrogen atoms.

5. The solid support as claimed in claim 1 wherein said lipophilic group comprises a cyclic group.

6. The solid support as claimed in claim 5 wherein said lipophilic group comprises two or more cyclic groups which are optionally fused.

7. The solid support as claimed in claim 1 wherein said lipophilic group is an R group of an amino acid.

8. The solid support as claimed in claim 7, wherein said amino acid is selected from the group comprising phenylalanine, tryptophan, tyrosine, tributyl tryptophan (Tbt), biphenylalanine, diphenylalanine and a biphenylalanine derivative.

9. The solid support as claimed in claim 1 wherein said lipophilic group comprises no more than 2 polar groups.

10. The solid support as claimed in claim 9, wherein said lipophilic group comprises no polar groups.

11. The solid support as claimed in claim 1 wherein said peptide comprise 3 amino acid moieties, wherein in any order, 2 of said amino acid moieties are cationic amino acids, and 1 of said amino acids is an amino acid with a large lipophilic R group, the R group having 14-27 non-hydrogen atoms.

12. The solid support as claimed in claim 1 wherein said peptide has the formula (V)

wherein, in any order, 2 of said AA (amino acid) moieties are cationic amino acids and 1 of said AA is an amino acid with a lipophilic R group, the R group having 14-27 non-hydrogen atoms;
   $R_1$ is a N atom, which may be substituted by a branched or unbranched $C_1$-$C_{10}$ alkyl or aryl group, which group may incorporate up to 2 heteroatoms selected from N, O and S; and
   $R_2$ is an aliphatic moiety having 2-20 non-hydrogen atoms, said moiety being linear, branched or cyclic.

13. A method of treating a biofilm-associated infection in a subject which comprises administering to said subject a solid support as claimed in claim 1.

14. The solid support as claimed in claim 5 wherein the cyclic group is an aromatic cyclic group.

15. The method as claimed in claim 13 wherein said infection is a chronic wound infection, native valve endocarditis, acute otitis media, chronic bacterial prostatitis, pneumonia, dental plaque, periodontitis, a biofilm infection in a respiratory disease, or a device related infection associated with implantable or prosthetic medical devices.

16. A method of inhibiting biofilm formation or removing a biofilm, said method comprising contacting said biofilm with a solid support as claimed in claim 1.

17. The method as claimed in claim 16, wherein said biofilm is present on a medical device.

18. The method as claimed in claim 13, wherein said biofilm comprises Gram positive bacteria.

19. The method as claimed in claim 18, wherein said Gram positive bacteria comprises *Staphylococcus*.

20. The method as claimed in claim 19, wherein said *Staphylococcus* is *S. haemolyticus*.

21. The method of claim 16 wherein said biofilm comprises Gram positive bacteria.

22. The method of claim 21 wherein said Gram positive bacteria comprises *Staphylococcus*.

23. The method of claim 22 wherein said *Staphylococcus* is *S. haemolyticus*.

* * * * *

SEQUENCE LISTING

```
<160> NUMBER OF SEQ ID NOS: 2

<210> SEQ ID NO 1
<211> LENGTH: 4
<212> TYPE: PRT
<213> ORGANISM: artificial
<220> FEATURE:
<223> OTHER INFORMATION: synthetic peptide
<220> FEATURE:
<221> NAME/KEY: MOD_RES
<222> LOCATION: (4)..(4)
<223> OTHER INFORMATION: NH-CH2CH2Ph

<400> SEQUENCE: 1

Arg Trp Trp Arg
1

<210> SEQ ID NO 2
<211> LENGTH: 5
<212> TYPE: PRT
<213> ORGANISM: artificial
<220> FEATURE:
<223> OTHER INFORMATION: synthetic peptide
<220> FEATURE:
<221> NAME/KEY: MOD_RES
<222> LOCATION: (5)..(5)
<223> OTHER INFORMATION: NH-CH2CH2Ph

<400> SEQUENCE: 2

Trp Arg Trp Trp Arg
1               5
```